United States Patent
Boussios et al.

(10) Patent No.: US 12,224,072 B2
(45) Date of Patent: *Feb. 11, 2025

(54) IDENTIFICATION OF PATIENT SUB-COHORTS AND CORRESPONDING QUANTITATIVE DEFINITIONS OF SUBTYPES AS A CLASSIFICATION SYSTEM FOR MEDICAL CONDITIONS

(71) Applicant: OM1, Inc., Boston, MA (US)

(72) Inventors: Constantinos Ioannis Boussios, Chelsea, MA (US); Jigar Bandaria, Medford, MA (US); Richard Gliklich, Weston, MA (US)

(73) Assignee: OM1, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/414,296

(22) Filed: Jan. 16, 2024

(65) Prior Publication Data

US 2024/0153647 A1 May 9, 2024

Related U.S. Application Data

(63) Continuation of application No. 18/520,664, filed on Nov. 28, 2023, now abandoned, which is a
(Continued)

(51) Int. Cl.
*G16H 50/70* (2018.01)
*G16H 10/60* (2018.01)

(52) U.S. Cl.
CPC .............. *G16H 50/70* (2018.01); *G16H 10/60* (2018.01)

(58) Field of Classification Search
CPC .................. G16H 50/70; G16H 10/60
See application file for complete search history.

(56) References Cited

U.S. PATENT DOCUMENTS

| 5,486,999 A | 1/1996 | Mebane |
| 5,508,912 A | 4/1996 | Schneiderman |

(Continued)

FOREIGN PATENT DOCUMENTS

| EP | 2 614 480 A2 | 7/2013 |
| WO | 00/57310 A1 | 9/2000 |

(Continued)

OTHER PUBLICATIONS

Awan, et al., "Machine Learning-Based Prediction of Heart Failure Readmission or Death: Implications of Choosing the Right Model and the Right Metrics", ESC Heart Failure, DOI: 10.1002/ehf2.12419, vol. 6, Feb. 27, 2019, pp. 428-435.

(Continued)

*Primary Examiner* — Jay M. Patel
(74) *Attorney, Agent, or Firm* — Peter Gordon

(57) ABSTRACT

A classification method and system for medical conditions based on the concept of subtypes, which are classes of patients whose medical fact patterns as analyzed in an N-dimensional space places them closer to other patients belonging to the same subtype than to patients who belong to different subtypes and, who share similar likelihood of certain specified outcomes. A computer system processes patient data for a plurality of patients from a set of patients called a cohort. The computer system processes the patient data for the cohort to group patients into sub-cohorts of similar patients, i.e., each sub-cohort includes patients who have similar medical fact patterns in their patient data. Patients in different sub-cohorts generally, but not necessarily, have significant differences in their patient data. The computer system generates quantitative definitions, describing the patients in the sub-cohorts.

30 Claims, 8 Drawing Sheets

Related U.S. Application Data continuation of application No. 16/724,264, filed on Dec. 21, 2019, now Pat. No. 11,862,346.

(60) Provisional application No. 62/784,434, filed on Dec. 22, 2018.

(56) References Cited

U.S. PATENT DOCUMENTS

| | | | |
|---|---|---|---|
| 5,619,421 A | 4/1997 | Venkataraman et al. | |
| 5,961,332 A | 10/1999 | Joao | |
| 6,101,511 A | 8/2000 | Derose et al. | |
| 6,317,731 B1 | 11/2001 | Luciano | |
| 6,524,241 B2 | 2/2003 | Iliff | |
| 6,687,685 B1 | 2/2004 | Sadeghi et al. | |
| 7,076,437 B1 | 7/2006 | Levy | |
| 7,194,301 B2 | 3/2007 | Jenkins et al. | |
| 7,433,519 B2 | 10/2008 | Rynderman | |
| 7,739,126 B1 | 6/2010 | Cave et al. | |
| 7,809,660 B2 | 10/2010 | Friedlander et al. | |
| 7,916,363 B2 | 3/2011 | Rynderman | |
| 7,930,262 B2 | 4/2011 | Friedlander et al. | |
| 7,949,620 B2 | 5/2011 | Otte et al. | |
| 8,090,590 B2 | 1/2012 | Fotsch et al. | |
| 8,140,541 B2 | 3/2012 | Koss | |
| 8,154,776 B2 | 4/2012 | Rynderman | |
| 8,165,973 B2 | 4/2012 | Alexe et al. | |
| 8,311,849 B2 | 11/2012 | Soto et al. | |
| 8,335,698 B2 | 12/2012 | Angell et al. | |
| 8,392,215 B2 | 3/2013 | Tawil | |
| 8,538,773 B2 | 9/2013 | Eddy et al. | |
| 8,560,281 B2 | 10/2013 | Soto et al. | |
| 8,583,586 B2 | 11/2013 | Ebadollahi et al. | |
| 8,930,223 B2 | 1/2015 | Friedlander et al. | |
| 9,514,416 B2 | 12/2016 | Lee et al. | |
| 9,646,271 B2 | 5/2017 | Friedlander et al. | |
| 9,690,844 B2 | 6/2017 | Mukherjee et al. | |
| 10,061,812 B2 | 8/2018 | Marshall et al. | |
| 10,282,512 B2 | 5/2019 | Bennett et al. | |
| 10,311,363 B1 | 6/2019 | Florissi et al. | |
| 10,311,975 B2 | 6/2019 | Young et al. | |
| 10,706,329 B2 | 7/2020 | Anushiravani et al. | |
| 10,731,223 B2 | 8/2020 | Kennedy et al. | |
| 10,731,233 B2 | 8/2020 | Yamada et al. | |
| 11,257,574 B1 | 2/2022 | Boussios et al. | |
| 11,527,326 B2 | 12/2022 | McNair et al. | |
| 11,594,310 B1 | 2/2023 | Bradley et al. | |
| 11,594,311 B1 | 2/2023 | Bradley et al. | |
| 11,862,346 B1 | 1/2024 | Boussios et al. | |
| 11,967,428 B1 | 4/2024 | Boussios et al. | |
| 12,057,204 B2 | 8/2024 | Bradley et al. | |
| 12,142,355 B2 | 11/2024 | Bradley et al. | |
| 2003/0014284 A1 | 1/2003 | Jones | |
| 2004/0122706 A1 | 6/2004 | Walker et al. | |
| 2004/0122707 A1 | 6/2004 | Sabol et al. | |
| 2004/0243362 A1 | 12/2004 | Liebman | |
| 2006/0058384 A1 | 3/2006 | Hogg | |
| 2006/0129427 A1 | 6/2006 | Wennberg | |
| 2006/0129428 A1 | 6/2006 | Wennberg | |
| 2006/0173663 A1 | 8/2006 | Langheier et al. | |
| 2007/0021979 A1 | 1/2007 | Cosentino et al. | |
| 2007/0172907 A1 | 7/2007 | Volker et al. | |
| 2007/0255113 A1 | 11/2007 | Grimes | |
| 2008/0171916 A1 | 7/2008 | Feder et al. | |
| 2008/0208813 A1 | 8/2008 | Friedlander et al. | |
| 2008/0235049 A1 | 9/2008 | Morita et al. | |
| 2008/0294459 A1 | 11/2008 | Angell et al. | |
| 2009/0119337 A1 | 5/2009 | Biedermann | |
| 2009/0164237 A1 | 6/2009 | Hunt et al. | |
| 2009/0259494 A1 | 10/2009 | Feder et al. | |
| 2009/0287503 A1 | 11/2009 | Angell et al. | |
| 2010/0021956 A1 | 1/2010 | Shearer et al. | |
| 2010/0191088 A1 | 7/2010 | Anderson et al. | |
| 2010/0240035 A1 | 9/2010 | Jablons et al. | |
| 2010/0324927 A1 | 12/2010 | Tinsley | |
| 2011/0010328 A1 | 1/2011 | Patel et al. | |
| 2011/0071363 A1 | 3/2011 | Montijo et al. | |
| 2011/0106558 A1 | 5/2011 | Solito et al. | |
| 2011/0125680 A1 | 5/2011 | Bosworth et al. | |
| 2011/0177956 A1 | 7/2011 | Korenberg | |
| 2011/0288877 A1* | 11/2011 | Ofek | G16H 50/20 707/661 |
| 2012/0065987 A1 | 3/2012 | Farooq et al. | |
| 2012/0084064 A1 | 4/2012 | Dzenis et al. | |
| 2012/0110016 A1* | 5/2012 | Phillips | G16Z 99/00 707/E17.014 |
| 2012/0179478 A1 | 7/2012 | Ross | |
| 2012/0191640 A1 | 7/2012 | Ebadollahi et al. | |
| 2012/0215560 A1* | 8/2012 | Ofek | G16H 70/20 705/3 |
| 2012/0254098 A1 | 10/2012 | Flinn et al. | |
| 2012/0296675 A1 | 11/2012 | Silverman | |
| 2013/0185231 A1 | 7/2013 | Baras et al. | |
| 2014/0006447 A1 | 1/2014 | Friedlander et al. | |
| 2014/0074510 A1 | 3/2014 | Mcclung et al. | |
| 2014/0081898 A1 | 3/2014 | Saigal et al. | |
| 2014/0095204 A1 | 4/2014 | Fung et al. | |
| 2014/0108044 A1 | 4/2014 | Reddy et al. | |
| 2014/0164022 A1 | 6/2014 | Reed et al. | |
| 2014/0249834 A1 | 9/2014 | D'Souza et al. | |
| 2014/0350954 A1* | 11/2014 | Ellis | G16H 10/60 705/2 |
| 2015/0106109 A1 | 4/2015 | Crowley et al. | |
| 2015/0106115 A1 | 4/2015 | Hu et al. | |
| 2015/0235001 A1 | 8/2015 | Fouts | |
| 2015/0339442 A1 | 11/2015 | Oleynik | |
| 2015/0347599 A1 | 12/2015 | McMains et al. | |
| 2016/0004840 A1 | 1/2016 | Rust et al. | |
| 2016/0012202 A1 | 1/2016 | Hu et al. | |
| 2016/0015347 A1 | 1/2016 | Bregman-Amitai et al. | |
| 2016/0029919 A1 | 2/2016 | Hebert et al. | |
| 2016/0078183 A1 | 3/2016 | Trygstad et al. | |
| 2016/0120481 A1 | 5/2016 | Li et al. | |
| 2016/0188814 A1 | 6/2016 | Raghavan et al. | |
| 2016/0188834 A1 | 6/2016 | Erdmann et al. | |
| 2016/0196394 A1 | 7/2016 | Chanthasiriphan et al. | |
| 2016/0235373 A1 | 8/2016 | Sharma et al. | |
| 2016/0283679 A1 | 9/2016 | Hu et al. | |
| 2016/0283686 A1 | 9/2016 | Hu et al. | |
| 2016/0354039 A1 | 12/2016 | Soto et al. | |
| 2017/0046602 A1 | 2/2017 | Hu et al. | |
| 2017/0061093 A1 | 3/2017 | Amarasingham et al. | |
| 2017/0124263 A1 | 5/2017 | Crafts et al. | |
| 2017/0124279 A1 | 5/2017 | Rothman | |
| 2017/0147777 A1 | 5/2017 | Kim et al. | |
| 2017/0235887 A1* | 8/2017 | Cox | G16H 10/60 705/3 |
| 2017/0262609 A1 | 9/2017 | Perlroth et al. | |
| 2017/0323075 A1 | 11/2017 | Krause et al. | |
| 2018/0268937 A1 | 9/2018 | Spetzler et al. | |
| 2018/0330805 A1 | 11/2018 | Cheung et al. | |
| 2018/0336319 A1 | 11/2018 | Itu et al. | |
| 2019/0079938 A1 | 3/2019 | Agrawal et al. | |
| 2019/0244714 A1 | 8/2019 | Morra et al. | |
| 2020/0411164 A1* | 12/2020 | Donner | G16H 30/20 |
| 2021/0098090 A1 | 4/2021 | Thomas et al. | |
| 2022/0148695 A1 | 5/2022 | Boussios et al. | |
| 2023/0197223 A1 | 6/2023 | Bradley et al. | |
| 2023/0197224 A1 | 6/2023 | Bradley et al. | |
| 2024/0096500 A1 | 3/2024 | Boussios et al. | |
| 2024/0290491 A1 | 8/2024 | Boussios et al. | |

FOREIGN PATENT DOCUMENTS

| | | |
|---|---|---|
| WO | 0209004 A1 | 1/2002 |
| WO | 02/09580 A1 | 2/2002 |
| WO | 03/104939 A2 | 12/2003 |
| WO | 2006/086181 A1 | 8/2006 |
| WO | 2007/050147 A1 | 5/2007 |
| WO | 2008/048662 A2 | 4/2008 |
| WO | 2008079341 A2 | 7/2008 |
| WO | 2012019000 A2 | 2/2012 |

(56) References Cited

FOREIGN PATENT DOCUMENTS

| | | |
|---|---|---|
| WO | 2014/028541 A1 | 2/2014 |
| WO | 2015169810 A1 | 11/2015 |

OTHER PUBLICATIONS

Bertens, et al., "A Nomogram was Developed to Enhance the use of Multinomial Logistic Regression Modeling in Diagnostic Research", Journal of Clinical Epidemiology, vol. 71, Mar. 2016, pp. 51-57.

Bodhe, et al., "A Proposed Mobile Based Health Care System for Patient Diagnosis using Android OS", International Journal of Computer Science and Mobile Computing, vol. 3 Issue.5, May 5, 2014, pp. 422-427.

Cheng, et al., "Risk Prediction with Electronic Health Records: A Deep Learning Approach", Proceedings of the SIAM International Conference on Data Mining, Jun. 2016, pp. 432-440.

Clockbackward, "Ordinary Least Squares Linear Regression: Flaws, Problems and Pitfalls", Jun. 18, 2009, 16 Pages.

Dua, et al., "Machine learning in healthcare informatics", vol. 56. Berlin: Springer, 2014, 334 Pages.

Grossman, et al., "Learning Bayesian Network Classifiers by Maximizing Conditional Likelihood", Proceedings of the 21st International Conference on Machine Learning, 2004, 8 Pages.

Hileman, "Accuracy of Claims-Based Risk Scoring Models", Society of Actuaries, Oct. 2016, pp. 1-90.

McCarthy, et al., "The Estimation of Sensitivity and Specificity of Clustered Binary Data", Statistics and Data Analysis, SUGI 31, Paper 206-31, 2006, 10 pages.

Mojsilovic, et al., "Semantic Based Categorization, Browsing and Retrieval in Medical Image Databases", Proceedings of the International Conference on Image Processing, IEEE, 2002, 2002, pp. 145-148.

Pearson, et al., "Disease Progression Modeling from Historical Clinical Databases", Proceedings of the Eleventh Acm Sigkdd International Conference on Knowledge Discovery in Data Mining, Aug. 21-24, 2005, pp. 788-793.

Ribeiro, "Why Should I Trust You?", Explaining the Predictions of Any Classifier, DOI: http://dx.doi.org/10.1145/2939672.2939778, Feb. 16, 2016, pp. 1135-1144.

Schneider, "Enabling Advanced Analytics to Improve Outcomes", Truven Health Analytics, Aug. 23, 2012, pp. 1-46.

Shen, "Using Cluster Analysis, Cluster Validation, and Consensus Clustering to Identify Subtypes of Pervasive Developmental Disorders", Queen's University, Nov. 2007, 119 Pages.

Soni, et al., "Using Associative Classifiers for Predictive Analysis in Health Care Data Mining", International Journal of Computer Applications (0975-8887), vol. 4, No. 5, Jul. 2010, pp. 33-37.

Su, et al., "Using Bayesian Networks to Discover Relations Between Genes, Environment, and Disease", Bio Data Mining, http://www.biodatamining.org/content/6/1/6, 2013, 21 Pages.

Suo, et al., "Risk Factor Analysis Based on Deep Learning Models", Proceedings of the 7th ACM International Conference on Bioinformatics, Computational Biology, and Health Informatics, Oct. 2-5, 2016, 10 Pages.

Tan, et al., "Cluster Analysis: Basic Concepts and Algorithms,", Introduction to Data Mining (Second Edition), Chapter 8, Feb. 2018, pp. 487-568.

Truven Health Analytics, "Flexible Analytics for Provider Evaluation", Solution Spotlight, 2017, 4 Pages.

Truven Health Analytics, "Modeling Studies: Published Articles and Presentations", 2016, pp. 1-6.

Truven Health Groups, "Enterprise Decision Support", Product Spotlight, 2012, 2 Pages.

U.S. Patent and Trademark Office, "Final Office Action Received", U.S. Appl. No. 15/465,542, filed Dec. 30, 2019, 54 Pages.

U.S. Patent and Trademark Office, "Final Office Action Received", U.S. Appl. No. 15/465,542, filed Jan. 4, 2022, 60 pages.

U.S. Patent and Trademark Office, "Final Office Action Received", U.S. Appl. No. 15/465,550, filed Mar. 21, 2022, 12 Pages.

U.S. Patent and Trademark Office, "Final Office Action Received", U.S. Appl. No. 16/386,123, filed Mar. 31, 2023, 59 Pages.

U.S. Patent and Trademark Office, "Final Office Action Received", U.S. Appl. No. 16/724,264, filed Nov. 30, 2022, 11 Pages.

U.S. Patent and Trademark Office, "Final Office Action Received", U.S. Appl. No. 15/927,766, filed Oct. 6, 2020, 22 Pages.

U.S. Patent and Trademark Office, "Final Office Action Received", U.S. Appl. No. 15/465,550, filed Oct. 14, 2020, 15 Pages.

U.S. Patent and Trademark Office, "Non Final Office Action Received", U.S. Appl. No. 15/927,766, filed Apr. 30, 2020, 19 Pages.

U.S. Patent and Trademark Office, "Non Final Office Action Received", U.S. Appl. No. 15/465,550, filed Jun. 26, 2019, 7 Pages.

U.S. Patent and Trademark Office, "Non Final Office Action Received", U.S. Appl. No. 16/386,123, filed Jun. 28, 2022, 55 Pages.

U.S. Patent and Trademark Office, "Non Final Office Action Received", U.S. Appl. No. 15/465,550, filed Mar. 13, 2020, 12 Pages.

U.S. Patent and Trademark Office, "Non Final Office Action Received", U.S. Appl. No. 15/465,542, filed Mar. 19, 2019, 29 Pages.

U.S. Patent and Trademark Office, "Non-Final Office Action Received", U.S. Appl. No. 15/465,542, filed Apr. 1, 2021, 73 Pages.

U.S. Patent and Trademark Office, "Non-Final Office Action Received", U.S. Appl. No. 15/465,550, filed Jul. 29, 2021, 31 Pages.

U.S. Patent and Trademark Office, "Non-Final Office Action Received", U.S. Appl. No. 18/169,363, filed Jul. 7, 2023, 48 Pages.

U.S. Patent and Trademark Office, "Non-Final Office Action Received", U.S. Appl. No. 16/724,264, filed Mar. 21, 2022, 20 Pages.

U.S. Patent and Trademark Office, "Notice of Allowance Received", U.S. Appl. No. 15/465,550, filed Aug. 16, 2022, 8 Pages.

U.S. Patent and Trademark Office, "Notice of Allowance Received", U.S. Appl. No. 15/465,542, filed Aug. 24, 2022, 11 Pages.

U.S. Patent and Trademark Office, "Notice of Allowance Received", U.S. Appl. No. 16/386,123, filed Dec. 13, 2023, 12 Pages.

U.S. Patent and Trademark Office, "Notice of Allowance Received", U.S. Appl. No. 15/465,550, filed Jan. 26, 2023, 8 Pages.

U.S. Patent and Trademark Office, "Notice of Allowance Received", U.S. Appl. No. 16/724,264, filed May 22, 2023, 8 Pages.

U.S. Patent and Trademark Office, "Notice of Allowance Received", U.S. Appl. No. 15/927,766, filed Oct. 14, 2021, 35 Pages.

U.S. Patent and Trademark Office, "Notice of Allowance Received", U.S. Appl. No. 15/465,542, filed Oct. 28, 2022, 12 Pages.

U.S. Patent and Trademark Office, "Notice of Allowance Received", U.S. Appl. No. 16/724,264, filed Sep. 6, 2023, 7 Pages.

U.S. Patent and Trademark Office, "Restriction Requirement Received", U.S. Appl. No. 16/724,264, filed Oct. 7, 2021, 6 Pages.

U.S. Patent and Trademark Office, "Non-Final Office Action Received", U.S. Appl. No. 18/169,372, filed May 8, 2024, 16 Pages.

U.S. Patent and Trademark Office, "Notice of Allowance Received", U.S. Appl. No. 18/169,363, filed Mar. 27, 2024, 10 Pages.

Voshaar, et al., "Calibration of the PROMIS Physical Function Item Bank in Dutch Patients with Rheumatoid Arthritis", PLOS ONE, vol. 9, Issue 3, Mar. 2014, pp. 1-11.

Zhong, Yizhen, et al., "Characterizing Design Patterns of EHR-Driven Phenotype Extraction Algorithms," in 2018 IEEE International Conference on Bioinformatics and Biomedicine (BIBM), Madrid, Spain, 2018, pp. 1143-1146, doi: 10.1109/BIBM.2018.8621240.

U.S. Patent and Trademark Office, "Non-Final Office Action Received", U.S. Appl. No. 18/596,720, filed Sep. 16, 2024, 37 Pages.

U.S. Patent and Trademark Office, "Non-Final Office Action Received", U.S. Appl. No. 17/573,725, filed Sep. 9, 2024, 27 Pages.

U.S. Patent and Trademark Office, "Notice of Allowability Received", U.S. Appl. No. 18/169,372, filed Oct. 16, 2024, 2 Pages.

U.S. Patent and Trademark Office, "Notice of Allowance Received", U.S. Appl. No. 18/169,372, filed Sep. 25, 2024, 9 Pages.

* cited by examiner

IDENTIFICATION OF PATIENT SUB-COHORTS AND CORRESPONDING QUANTITATIVE DEFINITIONS OF SUBTYPES AS A CLASSIFICATION SYSTEM FOR MEDICAL CONDITIONS

CROSS-REFERENCE TO RELATED APPLICATIONS

This application is a continuation of U.S. patent application Ser. No. 18/520,664, filed Nov. 28, 2023, entitled "IDENTIFICATION OF PATIENT SUB-COHORTS AND CORRESPONDING QUANTITATIVE DEFINITIONS OF SUBTYPES AS A CLASSIFICATION SYSTEM FOR MEDICAL CONDITIONS", which is a continuation of U.S. patent application Ser. No. 16/724,264, filed Dec. 19, 2021. entitled "IDENTIFICATION OF PATIENT SUB-COHORTS AND CORRESPONDING QUANTITATIVE DEFINITIONS OF SUBTYPES AS A CLASSIFICATION SYSTEM FOR MEDICAL CONDITIONS", which is a non-provisional application of U.S. Provisional Patent Application Ser. No. 62/784,434, filed Dec. 22, 2018, entitled "IDENTIFICATION AND QUANTITATIVE DEFINITION OF PATIENT SUBTYPES AND OUTCOMES AS A CLASSIFICATION SYSTEM FOR MEDICAL CONDITIONS AND DISEASES", which is hereby incorporated by reference.

BACKGROUND

Currently, diseases and health conditions often are described and defined by physicians and clinicians by identifying general fact patterns of symptoms, signs, laboratory results, imaging results, and other information, which patients having a disease or health condition are known to exhibit. Such information generally is collected from patients during clinical visits through patient histories, physical examinations, and tests. Such an approach to defining diseases and health conditions leverages human pattern recognition developed by training and experience. Sometimes collective experience is encapsulated in guidelines used by health care professionals.

Many diseases and health conditions are heterogeneous, meaning that patients with a given diagnosis have a range of characteristics that generally, but variably, overlap with fact patterns that correspond to the diagnosis. While in some cases there are definitive tests that can confirm a diagnosis, e.g., a viral titer to confirm a viral infection or a genetic test that confirms specific abnormalities such as Pompe Disease, many diseases and health conditions are defined by fact patterns that are multi-factored, experiential, and/or dependent on human judgment. Of course, treatments for patients, in turn, generally are based on the patients' diagnoses.

One limitation of current approaches to defining diseases and health conditions is that such definitions tend to be broad or imprecise, such as Type II diabetes, heart disease, and systemic lupus erythematosus.

A definition of a disease or health condition is broad when many diverse patients can meet its criteria. Current definitions of diseases or health conditions tend to be broad when they are based on only a few facts among many possible facts in patient data.

A definition of a disease or health condition can be imprecise in several ways. For example, different doctors could arrive at different diagnoses for the same patient. Or, a doctor may arrive at different diagnoses for different patients with similar medical histories. Current definitions of diseases or health conditions tend to be imprecise when they are partly based on general human recognition of patterns among patients based on experience, which may be captured in training and guidelines for health care professionals.

Using current broad definitions for diseases and health conditions, patients having the same disease or health condition will exhibit a broad range of characteristics, will have varying responses to various treatments, and will exhibit a range of outcomes such that some patients will have outcomes significantly different than other patients with the same disease or health condition, based on current definitions, and same treatment.

Using imprecise definitions for diseases and health conditions, diagnoses which, for example, may not properly account for comorbidities or parallel treatments for other conditions that the patient may be undergoing, may result in prescribed treatments that produce unforeseen side effects or suboptimal outcomes.

Because treatments for patients generally depend on their diagnoses, broad or imprecise diagnoses can lead to ineffective treatments and varying outcomes among patients, which in turn limits development of better treatments. These broad or imprecise definitions likely represent more than one disease or health condition.

Some computational techniques, typically called machine learning, deep learning, or artificial intelligence, have been used to develop models to classify patients as having a disease or health condition, based on current definitions of diseases and health conditions. These computational techniques still have the same drawbacks as having a health care provider classify a patient, because such a classification system uses the same labels for currently defined diseases and health conditions as health care providers do. In other words, if patient data is labeled based on current broad or imprecise definitions of diseases and health conditions, the resulting computational models classify patients as being in those broad or imprecise categories of diseases and health conditions. Second, these computational techniques generally result in opaque, "black box" solutions which do not help users of such techniques to understand how models are classifying patients, or what can be done to treat patients to improve their outcomes.

SUMMARY

This Summary introduces a selection of concepts in simplified form that are described further below in the Detailed Description. This Summary neither identifies features as key or essential, nor limits the scope of, the claimed subject matter.

A classification system for medical conditions is defined by a set of quantitative definitions of classes of patients, herein called subtypes. Each subtype has a subtype definition defined in an N-dimensional space which determines, given patient data for a patient, whether the patient belongs to the subtype. The subtype definition has an associated mapping defining how patient data is mapped to a patient vector representing the patient in the N-dimensional space in which the subtype is defined. Each subtype in the classification system defines a medical condition wherein patients belonging to the subtype have medical fact patterns that, when mapped to the N-dimensional space, are quantitatively closer to medical fact patterns of patients belonging to the subtype than to other patients belonging to other subtypes. Further, patients belonging to the subtype have a similar likelihood of a health care outcome.

These quantitative definitions are derived by, at first, identifying groups of patients, herein called sub-cohorts, such that the medical fact patterns of patients in each sub-cohort, as analyzed in the N-dimensional space, are closer to the patients in the sub-cohort than to patients in the other sub-cohorts. Given a set of identified sub-cohorts, sub-cohort level outcome statistics can be analyzed to determine which sub-cohorts are meaningful and represent a medically interesting subtype. Subtype definitions and associated mappings for medically interesting subtypes are stored as subtypes in the classification system, in which they can be applied to other patient data to determine whether other patients belong to these subtypes.

In one implementation, a computer system processes patient data for a plurality of patients from a set of patients called a cohort. The patient data generally includes, for each patient, one or more of demographic data about the patient, medical information for the patient, genotypic data for the patient, and lifestyle information of the patient. The computer system processes the patient data for the cohort to group patients into sub-cohorts of similar patients, i.e., each sub-cohort includes patients who have similar medical fact patterns in their patient data. These fact patterns also differ quantitatively from the medical fact patterns of patients in other sub-cohorts. Patients in different sub-cohorts generally, but not necessarily, have significant differences in their patient data, such that sub-cohorts are rarely overlapping. Within each sub-cohort, demographic data, medical history data, genotypic data, and lifestyle data of the patients include fact patterns which are more closely related quantitatively to each other than to fact patterns in data for other groups of patients.

The computer system generates a quantitative definition describing the patients in a sub-cohort based on facts which are common in the patient data within the sub-cohort. This quantitative definition is called herein a "subtype definition" which defines a "subtype". A subtype definition is quantitative because it represents the common facts for a class of patients defined by the subtype definition and because those fact patterns, when mapped to an N-dimensional space, are quantitatively closer to the fact patterns of other patients belonging to the same subtype than to the fact patterns of other patients belonging to other subtypes. The subtype definition is based on quantified patient data, even if some quantified data represents qualitative information about a patient, such as a broad or imprecise diagnosis based on current definitions of diseases and health conditions. The label for the class of patients meeting this definition is called herein a "subtype". Any patient for which the patient data at a given moment in time meets a subtype definition for a subtype belongs to that subtype for that moment in time.

Further associating subtypes with outcomes enables understanding how subtypes relate to outcomes. For example, the computer system can process outcome data for patients in each sub-cohort to determine whether there is a sub-cohort in which patients have outcomes that are meaningfully different from outcomes of patients in other sub-cohorts, in the entire cohort, or within a larger population. If outcomes for patients in a sub-cohort are meaningfully different from outcomes for other groups of patients, then the patients in the sub-cohort may belong to, as called herein, a "medically-interesting subtype". When outcome data is available for at least a subset of patients in a sub-cohort, the computer system can predict outcomes for one patient in the sub-cohort based on the outcomes for other patients in that sub-cohort.

The subtype definition for a medically interesting subtype not only provides a quantitative definition of that subtype, but also provides a definition of a medical condition which may be less broad or more precise than a currently used definition of a disease or health condition. Generally, a medically interesting subtype is defined using many factors, which results in the subtype representing a narrow subset of the patient population. Further, sources of imprecision can be attenuated because subtypes are defined by using quantified patient data both for many factors and from a long period of time within the patient's medical history. Because each subtype represents a class of patients having similar fact patterns in their patient data, the patients belonging to a medically interesting subtype may have a particular medical condition characterized by the subtype definition. That medical condition may be specified less broadly and more precisely by that subtype definition than by a currently used definition of a disease or health condition otherwise characterizing the patients in that subtype. To distinguish herein currently used definitions of diseases and health conditions from the label given a patient that belongs to a subtype, we refer herein to the patient belonging to a subtype as having a "medical condition characterized by the subtype", or "medical condition" for short. Because a medically-interesting subtype is identified based on outcome data, the medical condition characterized by a subtype also can be understood as being characterized by both the prevalent fact patterns in the patient data in the sub-cohort and the outcomes for the patients in the sub-cohort.

Because subtype definitions are generated from quantitative patient data, a subtype definition can be represented in a computer in a manner such that it can be read and interpreted as computer program instructions that, when executed on patient data, determine whether a patient belongs to a subtype. A computer system that generates subtype definitions thus generates computer programs for subtype membership detection. In other words, subtype definitions are effectively small computer programs that act as detectors of whether a patient, based on their patient data at a specific time, belongs to the corresponding subtype at that time. Subtype definitions can be distributed to and applied on other computer systems for application to other patient data, without requiring access either to the original patient data or to the computer system used to identify sub-cohorts or generate the subtype definitions.

When a patient is identified as belonging to a subtype, a variety of inferences can be made with respect to the patient, such as predicting outcomes, identifying treatments, and/or identifying risks for the patient, based on data for other patients belonging to that subtype. Various attributes associated with patients in a subtype also can be associated with a patient determined to be in that subtype.

Accordingly, in one aspect, a computer system includes components which identify sub-cohorts and subtypes, generate subtype definitions, collect subtype definitions into a classification system of medical conditions, or apply subtype definitions to determine whether a patient belongs to a particular subtype, or a combination of any two or more of such components. When outcome data is available, the computer system can include a component which identifies medically interesting subtypes. In some implementations, the computer system can include a component which makes inferences for a patient, based on whether the patient has been determined to belong to a subtype.

The following Detailed Description references the accompanying drawings which form a part this application, and which show, by way of illustration, specific example implementations. Other implementations may be made without departing from the scope of the disclosure.

DETAILED DESCRIPTION

Figure 1:
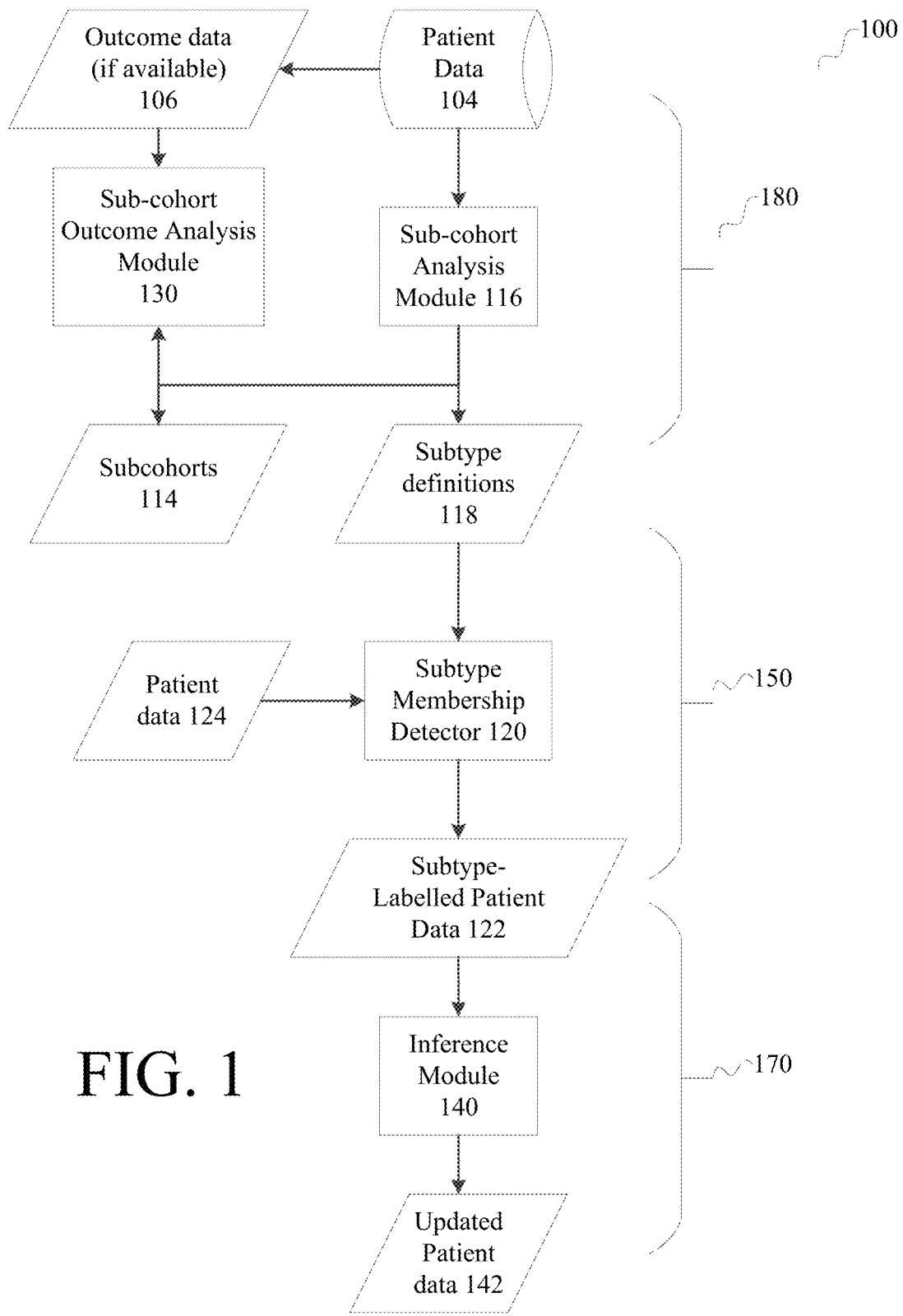
FIG. 1 is a data flow diagram of an example implementation of a computer system that generates and applies computer programs for subtype membership detection.

A classification system for medical conditions is defined by a set of quantitative definitions of classes of patients, herein called subtypes. Each subtype has a subtype definition defined in an N-dimensional space which determines, given patient data for a patient, whether the patient belongs to the subtype. The subtype definition has an associated mapping defining how patient data is mapped to a patient vector representing the patient in the N-dimensional space in which the subtype is defined. Each subtype in the classification system defines a medical condition wherein patients belonging to the subtype have medical fact patterns that, when mapped to the N-dimensional space, are quantitatively closer to medical fact patterns of patients belonging to the subtype than to other patients belonging to other subtypes. Further, patients belonging to the subtype have a similar likelihood of a health care outcome.

These quantitative definitions are derived by, at first, identifying groups of patients, herein called sub-cohorts, such that the medical fact patterns of patients in each sub-cohort, as analyzed in the N-dimensional space, are closer to the patients in the sub-cohort than to patients in the other sub-cohorts. In one implementation, referring to FIG. 1, a data flow diagram of an example implementation of a classification system for medical conditions will now be described.

A computer system 100 processes patient data 104 for a plurality of patients. The patient data generally includes, for each patient, one or more of demographic data about the patient, medical information for the patient, genotypic data for the patient, and lifestyle information of the patient. The patient data may include outcome data 106 for the patient. When outcome data for a plurality of patients is available, information such as outcome rates, average outcomes, expected outcomes, or any combination of two or more of these, can be computed for the plurality of patients.

Patient data can be obtained from a number of different sources of health care information for the patient including, but not limited to, electronic medical records from the patient's health care providers, insurance providers, and other sources.

More particularly, patient data can include, but is not limited to, information recorded for patients by a health care provider. Examples of health care providers include, but are not limited to, individuals, such as a physician, a therapist, a nurse, or support staff, and organizations, such a hospital or other facility employing health care providers. Patient data can include information from entities other than health care providers but who are otherwise involved in health care, such as insurers, pharmacies, laboratories, supply providers and the like, which may store information about claims, diagnostic tests, laboratory work, supplies, and vendors. Patient data can include information reported by patients or their caregivers or both.

The medical information can include any one or more of, for example, information about reported or observed symptoms of the patient, diagnoses made by the health care provider, any medications, treatments, or other interventions prescribed or recommended by the health care provider, or any requests for laboratory work or diagnostic tests and related reports or results, or any other information about encounters with health care providers. Such data can be stored as a history of interactions or encounters with the health care provider and may have multiple instances of a type of data over time, such as vital signs and lab results. Such data typically includes information, typically representing symptoms, diagnoses, procedures and medications, which is typically coded according to a standard, such as ICD-9, ICD-10, CPT, SNOMED, LOINC, COSTAR, and RxNorm coding systems.

The demographic information can include, for example, age, gender, race, family history, social history, and other information for the patient. If there is authorization to store personally identifying information, then such information may include a name, an address and various contact information.

Genotypic information can include data representing information about genetic profiles of patients.

Lifestyle information can include data representing information about aspects of patients' daily lives that can affect their health, such as smoking history, exercise type and frequency, diet information, occupation, family status, socioeconomic status, family history of disease, and so on.

The patient data generally is stored as a set of occurrences of events. Each recorded event occurs at a point in time in a history of events for the patient. For some types of events, a relative time can be computed with respect to a reference time and stored.

Patient data can be de-identified data such that any personally identifying information is removed, in which case patient data for a patient is associated with a unique code representing that patient, which code distinguishes the patient from other patients.

Patient data generally includes both structured and unstructured data. Structured data generally is data that has a specified data model or other organization, whereas unstructured data generally does not. By way of example, structured data can include database records, attribute-value pairs, and the like, whereas unstructured data can be either textual data, such as free text, documents, reports of results, published and unpublished literature, and the like, or non-textual data, such as image data of which DICOM data is an example.

Patient data also can include cost information related to resources for various activities related to providing health care for a patient. Thus, for each activity performed with respect to a patient, resource utilization information also can be made available. Resources can include personnel, equipment, supplies, space, and the like. Resources generally have an associated cost, typically represented by a cost per unit, cost per unit of time, cost per unit of space, and the like.

The computer system includes a sub-cohort analysis module 116 which, given the patient data 104, generates subtype definitions 118. The sub-cohort analysis module processes the patient data 104 to select a set of patients called a cohort. The computer system processes the patient data for the cohort to group patients into sub-cohorts 114 of similar patients, i.e., each sub-cohort includes patients who have similar fact patterns in their patient data. Patients in different sub-cohorts generally, but not necessarily, have significant differences in their patient data. Within each sub-cohort, one or more of the demographic data, medical history data, genotypic data, and lifestyle data of the patients include fact patterns which are more closely related quantitatively to each other than to fact patterns in the data for other groups of patients, according to criteria of similarity used to identify the sub-cohorts.

The computer system generates, for a sub-cohort, a quantitative definition describing the patients in the sub-cohort based on facts which are common in the patient data within the sub-cohort. This quantitative definition is called herein a "subtype definition" which defines a "subtype". A subtype definition is quantitative because it represents the common facts for a class of patients defined by the subtype definition and those fact patterns, when mapped to an N-dimensional space, are quantitatively closer to the fact patterns of other patients belonging to the same subtype than to the fact patterns of other patients belonging to other subtypes. The subtype definition is based on quantified patient data, even if some quantified data represents qualitative information about a patient, such as a broad or imprecise diagnosis based on current definitions of diseases and health conditions. The label for the class of patients meeting this definition is called herein a "subtype". Any patient for which the patient data at a given moment in time meets a subtype definition for a subtype belongs to that subtype for that moment in time. These definitions are output as subtype definitions 118.

Further associating subtypes with outcomes enables understanding how subtypes relate to outcomes. For example, a sub-cohort outcome analysis module 130 can process outcome data 106 for patients in sub-cohorts 114 to determine whether there is a sub-cohort in which patients have outcomes that are meaningfully different from outcomes of patients in other sub-cohorts, in the entire cohort, or within a larger population. If outcomes for patients in a sub-cohort are meaningfully different from outcomes for other groups of patients, then the patients in the sub-cohort may belong to, as called herein, a "medically-interesting subtype". When outcome data 106 is available for at least a subset of patients in a sub-cohort, the sub-cohort outcome analysis module 130 also can predict outcomes for other patients in the sub-cohort based on the outcomes for that subset of patients.

The subtype definition 118 for a medically interesting subtype not only provides a quantitative definition of that subtype, but also provides a definition of a medical condition which may be less broad or more precise than a currently used definition of a disease or health condition. Generally, a medically interesting subtype is defined using many factors, which results in the subtype representing a narrow subset of the patient population. Further, sources of imprecision can be attenuated because subtypes are defined by using quantified patient data both for many factors and from a long period of time within the patient's medical history. Because each subtype represents a class of patients having similar fact patterns in their patient data, the patients belonging to a medically interesting subtype may have a particular medical condition characterized by the subtype definition. That medical condition may be specified less broadly and more precisely by that subtype definition than by a currently used definition of a disease or health condition otherwise characterizing the patients in that subtype. To distinguish herein currently used definitions of diseases and health conditions from the label given a patient that belongs to a subtype, we refer herein to the patient belonging to a subtype as having a "medical condition characterized by the subtype", or "medical condition" for short. Because a medically-interesting subtype is identified based on outcome data, the medical condition characterized by a subtype also can be understood as being characterized by both the prevalent fact patterns in the patient data in the sub-cohort and the outcomes for the patients in the sub-cohort.

Because subtype definitions are generated from quantitative patient data, a subtype definition 118 can be represented in the computer system 100 in a manner such that it be read and interpreted as computer program instructions that, when executed on patient data, determines whether a patient belongs to the subtype. A computer system that generates subtype definitions 118 thus generates computer programs for subtype membership detection. In other words, subtype definitions are effectively small computer programs that act as detectors 120 of whether a patient, based on their patient data at a specific time, belongs to the corresponding subtype at that time. The subtype definitions 118 can be distributed to and applied on other computer systems 150, separate from computer system 100, for application to other patient data 124 for application to the other patient data, without requiring access either to the original patient data 104, 106 or to the computer system 180 (or more specifically, the sub-cohort analysis module 116) used to identify sub-cohorts 114 or generate the subtype definitions 118.

A subtype membership detector 120 uses the subtype definition 118 as a computer program to process patient data 124 for a patient, to determine whether the patient belongs to that subtype. Patient data 124 can originate from any other computer system, or from patient data 104. The subtype membership detector 120 can output data indicating the subtype to which the patient belongs, such as in the form of labeled patient data 122. The output indication can be stored with the patient data 124, or 104, or both, to which it corresponds.

Generally, to process patient data 124 using the subtype definition 118, the structure and content of the patient data (i.e., its structure, including field names and data types) should match the structure and content of data used in the subtype definition. This condition may be met in several ways, examples of which are the following. The patient data 124 has the same structure and content as data in the subtype definition 118. The patient data 104 has the same content, and is transformed to have the same structure, as data in the subtype definition 118. The data in the subtype definition 118 is transformed to have the same structure as the patient data. The subtype definition 118 is defined in a manner that allows the subtype definition to be applied to data with different structures, such as the patient data 124.

When a patient is identified as belonging to a subtype, several inferences can be made with respect to the patient, as performed by the inference module 140 in FIG. 1. Several inferences can be performed, such as one or more of predicting or evaluating outcomes, identifying treatments, or identifying or evaluating risks for the patient. Some inferences can be based on data for other patients belonging to that subtype. Attributes generally associated with patients in a subtype also can be associated with a patient determined to be in that subtype. One or more of outcome data, treatment information, risk information, or attribute data can be output by the inference module, for example in the form of updated patient data 142. Such outputs can be stored in the original patient data 124, 104.

The inference module 140, subtype membership detector 120, and analysis modules 116, 130 can be implemented on different computer systems, indicated by 170, 150, and 180, respectively, or may be combined onto one or more computer systems.

Figure 2:
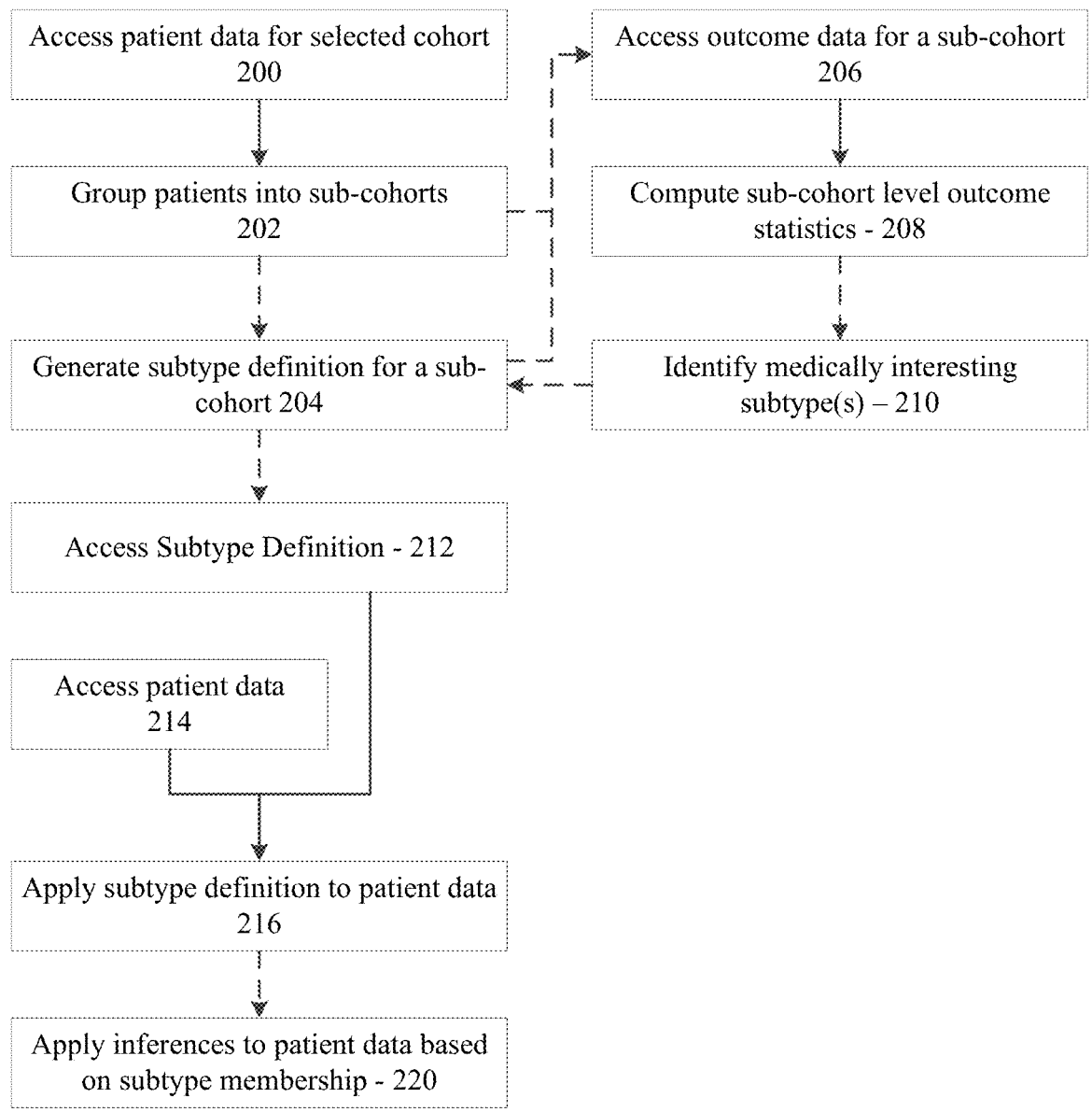
FIG. 2 is a flow chart describing operations using a computer system such as in FIG. 1.

Computer-implemented processes using such a computer system are illustrated by the flowcharts of FIG. 2. In FIG. 2, dashed lines between sets of steps indicate that the processes represented by these sets of steps can be performed at different times, by different entities, or using different computer systems.

In a first set of steps, a computer system accesses 200 patient data for a cohort selected from a set of patients. This cohort can be called a training cohort. The sub-cohort analysis module (116 in FIG. 1) groups 202 the patients into sub-cohorts of similar patients based on fact patterns in their patient data. The sub-cohort analysis module generates 204 a subtype definition for a sub-cohort based on facts which are common in the patient data for patients within the sub-cohort. Subtype definitions can be generated for one, some or all of the sub-cohorts. Generation of a subtype definition for a sub-cohort can be deferred, for example, until outcome analysis for the sub-cohort indicates that the sub-cohort represents a medically interesting subtype.

If outcome data is available, the sub-cohort outcome analysis module (130 in FIG. 1) accesses 206 patient data for patients in one or more sub-cohorts. This module computes 208 sub-cohort level outcome statistics for a sub-cohort based on the patient data for patients in that sub-cohort. The sub-cohort level outcome statistics computed using this module can be used, for example, to identify 210 medically interesting subtypes. The sub-cohort level outcome statistics for a sub-cohort can be compared to the sub-cohort level outcome statistics for one or more of other groups of patients, such as the training cohort, any other cohort, another sub-cohort, or the general population, or can be compared to known norms, or any combination of these. As indicated by the dashed arrows in FIG. 2, the outcome analysis for a sub-cohort can occur at any time after a sub-cohort is identified, whether or not a subtype definition has been or will be generated for the sub-cohort. The computer system performing the outcome analysis in steps 206 through 210 can be independent of any computer system performing steps 200 through 204 and 212 through 220. Medically interesting subtypes can be identified at any time after sub-cohort level outcome statistics have been computed for a sub-cohort and can be performed using a separate computer system from the computer system used to compute the sub-cohort level outcome statistics.

To apply a subtype definition to determine whether a patient belongs in a subtype, a subtype membership detector (120 in FIG. 1) accesses 212 the subtype definition and accesses 214 patient data for the patient. These steps can be performed independently of each other and in any sequence or in parallel. Data for multiple patients can be accessed. The detector 120 applies 216 the subtype definition to the accessed patient data. Note that the performance of steps 212 through 216 by a subtype membership detector 120 can occur at any time after a subtype definition is generated, and the computer system implementing the subtype membership detector can be independent of any other computer system performing any of the steps 200 through 204, or steps 206 through 210, or step 220.

At any time after a patient's data has been processed to determine their subtype membership, various inferences can be made. An inference module (140 in FIG. 1) applies 220 inferences to the patient data based on the patient's subtype membership. To do so the inference module may access other data, such as one or more of outcome data, outcome statistics, or other information, or combinations thereof, to make such inferences. The inference module can be implemented using a computer system which is separate from the computer system that implements the subtype membership detector and can be used at any time independently of other parts of the computer system.

Figure 3:
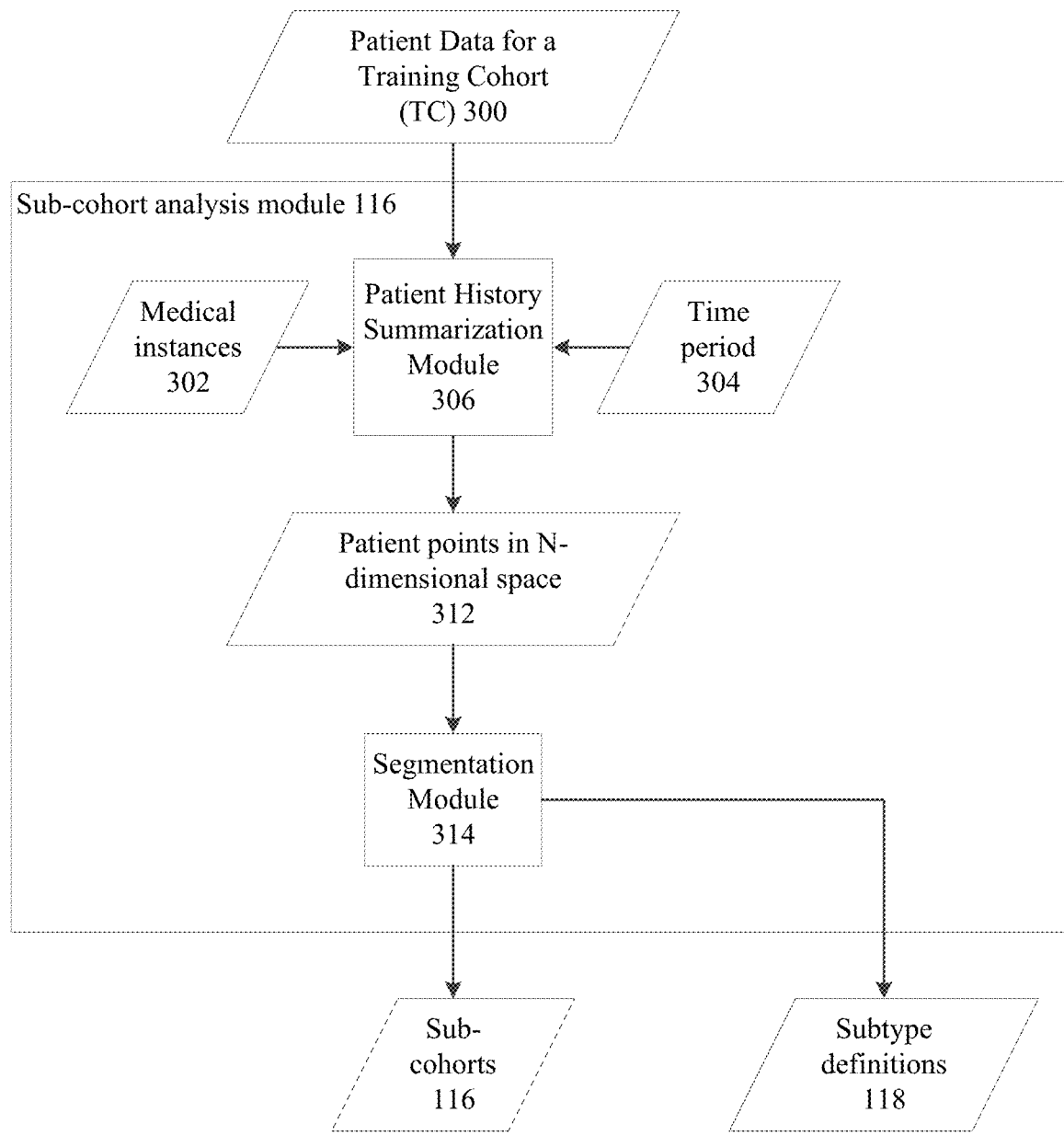
FIG. 3 is a data flow diagram describing an example implementation of a sub-cohort analysis module.
Figure 4:
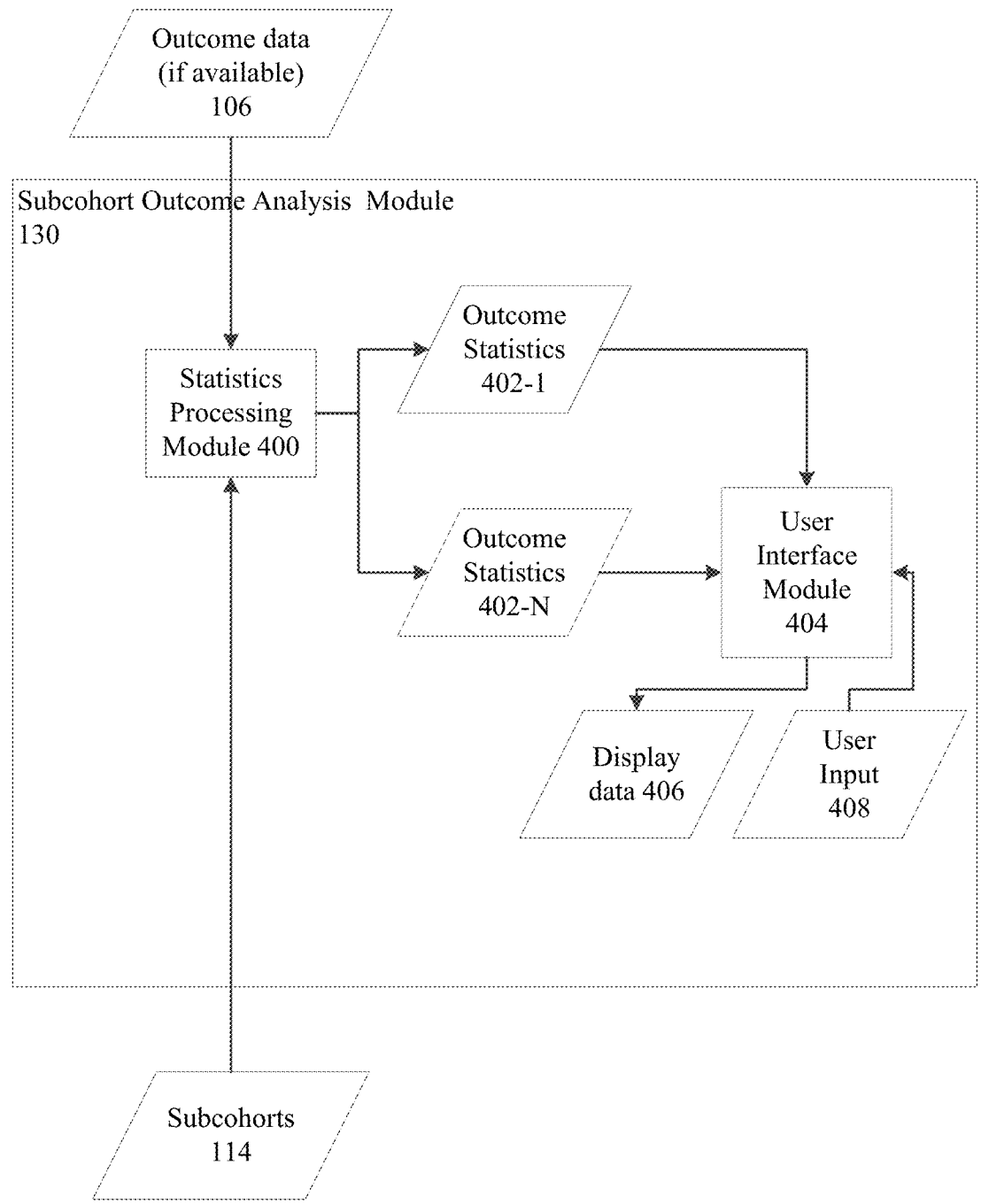
FIG. 4 is a data flow diagram describing an example implementation of sub-cohort outcome analysis module.

The steps in FIG. 2 and modules in the computer system in FIG. 1, will be described in more detail below in connection with an example implementation of such, as illustrated in FIGS. 3 and 4, for deriving subtypes, and illustrated in FIG. 6, for applying subtypes to patient data to determine subtypes to which patients belong.

In this example implementation, we refer to an item of patient data as a "medical event" (sometimes abbreviated herein as "ME"). A medical event is, generally, any item of data in the patient data. Patient data generally includes a collection of such medical events for each patient. Any kind of data, whether demographic data, medical information, genotypic data, or lifestyle data, can be stored in the computer system as a kind of medical event.

For the purpose of illustration, the following are a few non-limiting examples of medical events:

1. A diagnosis code, which indicates that a patient was assigned a code representing a diagnosis, such as an ICD9 code, at a certain time in the patient history.
2. A procedure code, which indicates that a patient experienced one of a procedure, test, laboratory, imaging, or other encounter with the health care system at a certain time.
3. A medication code, which indicates that a medication was prescribed by a prescriber or filled by a pharmacy at a certain time.
4. A medication dosage amount, which indicates a recommended amount and frequency for taking a medication.
5. A medication dosage era, which indicates an amount of medication likely consumed by a patient over a specified time interval. The amount can be estimated from an individual source, or a combination of sources, including, but not limited to, the specified dosing and amount prescribed by a prescriber over a specific period of time, the specified dosing and amount filled by pharmacies over a specific period of time, the specified dosing and amount infused at an infusion center over a specific period of time, and the labelled dosing and amount purchased from a retail pharmacy over a specific period of time.
6. A laboratory order code, which indicates a specific test and when the specific test was ordered.
7. A laboratory result code, which indicates a result for a specific test. For a laboratory result event in a patient history, the combination of the type of test and result value can be mapped to the appropriate laboratory result code which enters the patient history at the specific time. The laboratory order code and a laboratory result value can be combined into laboratory result value bins. In some implementations there could be two bins per type of laboratory result: normal and abnormal. In some implementations, more than two bins can be specified. Laboratory results can be entered as continuous variables in some implementations.

8. Imaging and other interpreted test findings, such as electrocardiograms. These events can include both qualitative information, such as specific findings, and quantitative information, such as number of new lesions, tumor dimensions, or specific flow rates. Such data in some instances can be transformed to value bins. Other methods of using imaging and related types of data, such as with 2-dimensional or 3-dimensional or time sequences, include classifying the interpretation of the test from binary results (such as normal, abnormal) to a finite set of results (single vessels, two vessels, and three vessels occluded). In this case, the type of test is combined with the result of the test to give image-result codes, which then enter the patient data in similar ways as labs and medications.

As an example implementation of medical events, a medical event can be represented using at least one field. A field is a data structure that stores a data value, and generally has a name and a data type. In object-oriented programming, a field is the data encapsulated within a class or object. Fields may be shared by multiple instances of an object. In relational databases, a field is the intersection of a row and a column, and the field name is the column name.

In such an implementation, a medical event generally comprises a code field to store a code, optionally one or more value fields to store corresponding values, and optionally a time stamp field to store a corresponding time stamp. Thus, any medical information can be represented as a medical event with a code field, an optional value field, and an optional time stamp field. For example, a medical event for a patient may be a diagnosis of a disease or health condition using current definitions, which can be represented by the combination of a code field storing the ICD10 code for the diagnosis, and a time stamp field storing the date and time a health care provider input the diagnosis into the patient data. As another example, a medical event for a patient may indicate a laboratory test, which can be represented by the combination of a code field storing a code representing the laboratory test, a value field storing a value for a result from the laboratory test, and a time stamp field storing a date the laboratory test was performed, or when the result was added to the patient data, or other relevant time.

A problem that can arise when processing a large volume of patient data is that the same fact can be stored in different ways for different patients and for a single patient. In other words, the same fact may be represented inconsistently throughout the data set. For example, different codes may be used, but may represent the same thing or generally similar things. There may be different codes for different medications which are in the same class of medications, such as pain medication. There may be different codes for different variants of a procedure, such as a left knee surgery versus a right knee surgery, when both are forms of knee surgery. Or, medical events that typically occur together, such as both a diagnosis and its corresponding laboratory test, may not appear together in a patient's data, e.g., there may be only a diagnosis code or only a laboratory test code. If the same fact is not represented in the same way, then it becomes difficult to identify patients that have similar fact patterns in their patient data.

Another problem that can arise when processing a large volume of patient data to identify sub-cohorts is that processing complexity increases with each additional dimension of patient data. If every kind of medical event is considered a dimension of the patient data, then the number of dimensions of data can become very large.

To address these problems, the computer system can process medical events into corresponding "medical instances", by applying a set of "medical instance mappings" to the medical events. Medical instances, in essence, "roll up" or "generalize" specific types of medical events by converting them into a more general type of medical instance. In general, a "medical instance mapping" is an operation performed on patient data that maps a medical event to a corresponding medical instance. The computer system can process medical events in patient data using medical instance mappings to compute corresponding medical instances. Data representing a medical instance can be stored in data structures similar to the data structures used for storing medical events. By generalizing specific types of medical events into a more general type of medical instance, the number of dimensions of patient data is reduced. Similarly, by mapping different types of medical events that represent the same fact into the same type of medical instance, the inconsistency in the data is reduced.

As one example, the computer system can use a mapping of a larger set of codes, that can occur in medical events, to a smaller set of codes used for the medical instances. For example, all codes in medical events representing different forms of pain medication can be mapped to a single new code as a medical instance representing those forms of pain medications.

As another example, the computer system can map a range of values stored in association with a code in medical events to smaller set of discrete ranges using medical instances. For example, different medical events can store different dosages for the same medication; the different dosages can be mapped to discrete ranges (e.g., low, medium, high).

The computer system can include one or more processes for deriving medical instance mappings.

For the purpose of illustration, given a set of medical events, there are several ways in which medical instances and their corresponding mappings can be derived. In one implementation, an MI can represent a single ME. In another implementation, an MI can represent a group of ME's. An entire set of individual ME's can be transformed into a finite, smaller set of such groups. Example approaches to deriving such mappings of medical events into medical instances include, but are not limited to, the following.

One approach uses medical instances that represent groups of medical codes. Each medical instance represents a set of codes which are related to each other in some way. In one implementation, the relation between codes within a medical instance could be a type of the codes. For example, all ICD10 Diagnosis codes, or a subset of such codes, could be represented by a medical instance; all CPT Procedure codes, or a subset of such codes, could be represented by another medical instance, etc. In this example, one mapping is defined that maps each ICD10 diagnosis code to a single code representing the medical instance; another mapping is defined that maps each CPT procedure code to another medical instance. This way of defining medical instances results in few medical instances, where the codes represented by each medical instance are related to each other by the type of the codes.

Another approach for defining medical instances is based on the relation of co-occurrence. Using this approach, a medical instance represents a collection of codes which co-occur in patient medical histories more frequently with each other than they co-occur with codes which are used to define other medical instances. The mapping maps each code in this collection of codes to the medical instance representing the collection of codes.

A computer system can include one or more computer program modules that implement various algorithms that can be used to derive a set of medical instances. For example, such a module can optimize grouping of codes with regards to co-occurrence. Different modules can implement different techniques for discovering different groups of codes that can be represented by different medical instances and deriving a mapping for that medical instance.

An example implementation of such a computer program module, which derives medical instances based on co-occurrence, utilizes a mapping algorithm, an example of which is known as "word2vec". Such algorithms may come in various forms, for example the Continuous Bag-of-Words model (CBOW) or the Skip-Gram model or other variations. The algorithm processes a set of patient medical histories for a plurality of patients. Each patient medical history is organized and represented as an ordered sequence of events, in which events are ordered with respect to time at which they occurred in the patient medical history. Such ordering sometimes cannot be strict due to multiple codes having identical timestamps. In that case, there can be a secondary ordering based on, for example, some other criteria (e.g., by type of code) or simply random secondary ordering. After the patient medical histories are ordered, the algorithm maps each code in the list of codes onto a Euclidean embedding space for which dimensions have been predetermined by the user. The algorithm, in this implementation word2vec, optimizes the mapping such that the more frequently two codes co-occur (i.e., are found in high proximity to each other) in patient medical histories, the closer their mapped embeddings reside in the embeddings space.

After such embeddings have been produced, medical instances can be produced by splitting the embeddings space into sub-spaces, each of which holds a cluster of embeddings. Such splitting can be produced by using Unsupervised Learning methods from the fields of Machine Learning, Statistical Learning, Artificial Intelligence, Deep Learning or combinations thereof. Unsupervised Learning is a collection of clustering algorithms which optimally split up the Euclidean embeddings space in subspaces by drawing a number of hypersurfaces which serve as the boundaries of the various subspaces. The number of resulting subspaces can be either pre-specified by the user or optimally selected by the clustering algorithm, depending on the use case and/or the algorithm. There is a large variety of clustering algorithms, as discussed above. Examples include k-means, k-medians, Expectation Maximization clustering using Gaussian Mixture Models, Agglomerative Hierarchical Clustering, Density-Based Spatial Clustering of Applications with Noise (DBSCAN), Deep Embedded Clustering and many others. Each one of these algorithms can be used to derive medical instances. In one implementation, the word2vec algorithm and k-means clustering can be used to derive medical instances.

Other implementations which derive medical instances on the basis of co-occurrence relations include algorithms derived from approaches such as count-based methods (e.g., Latent Semantic Analysis), and predictive methods (e.g., neural probabilistic language models). Word2vec is a predictive method. The methods of representation that use co-occurrence relations have the underlying hypothesis that medical codes which appear in the same patient medical histories relate to similar medical context or, in other words, similar conditions.

Relations other than co-occurrence of medical events in patient medical histories can be used to guide the automated derivation of medical instances that are groups of medical codes or events. Different algorithms from Artificial Intelligence, Machine Learning, Deep Learning may be used to derive medical instances based on such relations.

Medical instances also can be derived by human experts fully or partly. In that case, the medical experts use criteria that guide them to group codes into medical instances. For example, the criterion may be to ensure that codes which relate to the same condition are in the same group. A variety of criteria may guide human experts in their derivation of medical instances.

There are cases where medical instances can be derived using a combination of algorithms and human expertise. Human experts can adjust or alter medical instances derived by the computer, or can pre-process the data that is used by automated algorithms to derive the medical instances.

In another implementation, the set of derived medical instances may be algorithmically altered and fine-tuned using algorithms that might judiciously rearrange the medical event content of specific medical instances; or merge some medical instances into larger medical instances using same relation criteria as the ones used to derive the original set of medical instances or different relation criteria; or divide some medical instances to smaller medical instances in order to satisfy size or coherence criteria.

The various derivation methods described above result in a set of mappings that map medical events to the medical instances. This set of mappings can be organized in a library of medical instances. This library thus contains the building blocks of the patient sub-cohorts and corresponding subtypes that will be generated. A medical instance mapping module maps the patient data for patients in the training cohort into the medical instances based on the medical instance definitions accessed from the library. The library can be structured to include the following information for each medical instance:
  a. Set of medical events that are members of the medical instance;
  b. Any functions or other operation used to combine or process one or more of the medical events;
  c. A label or a key for uniquely identifying the medical instance; and
  d. A human-readable description of the medical instance, for example generated by medical experts and aiming at communicating the nature of the medical instance to users.

Referring back to FIG. 1, the computer system includes a sub-cohort analysis module 116 which processes patient data to identify sub-cohorts 114 and generate subtype definitions 118 for those sub-cohorts based on the patient data in those sub-cohorts. An example implementation of the sub-cohort analysis module will now be described in connection with FIG. 3. For the purposes of the rest of this description, the term "medical instance" is used, but should be understood to include medical events, or medical instances derived from medical events, or some combination of both. Sub-cohorts are identified based on the principle that similar medical histories tend to include similar medical instances.

In FIG. 3, the sub-cohort analysis module accesses patient data 300 for patients in a training cohort (TC) to groups those patients into sub-cohorts based on medical instances 302 and one or more time periods 304. In this implementation, the sub-cohort analysis module 116 includes a patient history summarization module 306 that summarizes medical instances occurring in patient histories during the specified time period 304. The time period 304 can be selected in many ways, with some examples described in more detail below.

Summarization of Patient History

Time Period 304

All of the patient data for a patient over time is called the patient history. This patient history is summarized over a selected time period 304. For a patient, the history can be summarized over a longer or shorter Time Period (TP) 304 than other patients. There are many ways to define the time period. The time period can be, for example, the entire lifetime from birth up to a certain date. The time period can be, for example, a specific period between two fixed time points. The time period can be a time period anchored on one event or between two events, for example, between two doctor visits, or a time period before, or after, or around a surgical operation. The time period can be the union of multiple periods that are disjoint.

History Representation

Generally, a patient history is summarized by mapping patient data into an N-dimensional space, such as an N-dimensional patient vector representing the patient. The mapping, in general, reflects the prevalence of certain characteristics, whether medical events, medical instances or other patient data, in the patient history. Each characteristic of the patient history to be considered is a dimension of the N-dimensional space. The value for a given patient for that characteristic represents the prevalence or relative prevalence of that characteristic in the patient's history. Note that the patient history summarization for a patient may change over time depending on how the time period 304 is defined, and due to the fact that patient histories change over time as patient data is added.

Considering an implementation in which each patient medical history over the time period 304 is a sequence of codes, one summarization of a patient history is a patient vector. Each medical instance can be one of the N dimensions of the patient vector. Given such a patient vector, the patient history can be summarized in several ways.

For example, the summarization of the patient history in the patient vector can be one count per member of the finite set of medical instances. If a certain medical instance appears k times in the patient history, then the corresponding position of that medical instance in the vector for that patient has the value k.

Another summarization may include computing a time weighted sum of each medical instance, where time is relative with respect to an anchor date. For example, the anchor date may be the date of an observation in the patient history.

Another summarization may include prevalence of a medical instance in the patient history relative to the prevalence of the medical instance in the collective patient history of a large patient population, of which the patient of interest is a member.

Let the summarization include N summary components as described above. Thus, the patient representation is a N-dimensional History Representation Vector (N-dHRV). Thus, for the patients in the training cohort, the patient history summarization module 306 outputs, for each patient, a point or patient vector in an N-dimensional space, as indicated at 312.

Enrichment with Demographic, Genotypic, and Lifestyle Data

In one implementation, the medical information of the patient can be augmented with additional facts such as demographic information, genotypic information, or lifestyle information, or any combination of these. Each one of these components can be converted to a Euclidean vector representation in order to be added on to the N-dHRV.

While the term N-dHRV is used herein, this term also includes additional patient descriptors that may not vary over time, in addition to those that do vary over time, such as age or the summary components described above.

Sub-Cohort Derivation

A set of patients is selected as the training cohort 300. The training cohort is chosen to satisfy use-case criteria such as the type of patient for which subtypes will be derived. One example is the set of patients who have certain conventional diagnosis codes in their medical history such as diabetes mellitus or certain demographic characteristics such as age. Another example is the set of patients for whom there is a certain confidence in the completeness of their medical history data available in the patient database, such as a minimum of enrollment to a health care plan.

Given the training cohort 300, medical instances 302, and time period 304, the patient vectors for the patients in the training cohort can be computed, which then can be segmented into sub-cohorts. As an example, for each patient in the training cohort:

Step 1. Assign a time period TP 304 for each patient in the TC, over which the N-dHRV 312 will be derived. In one implementation, the TP is identical among all patients. The TP could be defined by a fixed start date and a fixed end date, e.g., 1/1/2015-12/31/2015. Or it could be the union of two or more fixed intervals in their history, e.g., the union of the interval 1/1/2013-12/31/2013 and the interval 1/1/2015-12/31/2015. In another implementation, the TP can differ in length among patients.

One example is that the beginning of the TP is anchored at a specific event, e.g., on the day of a surgical operation. The end of the TP could be at a fixed time post the beginning of the TP, e.g., 30 days after the operation. The end of the TP in this example also could be anchored related to a specific event, e.g., on the day of hospital discharge after the surgical operation. The latter would generally result in TP's of varying length over patients in the TC. In that case, the more appropriate summarization of patient history might be a summarization based on MI prevalence as opposed to counts.

Another example is that the TP covers the entire patient history of each patient. Or other TP definition methods which result in unequal, varying TP lengths for over patients in the TC. Again, in this case MI prevalence summarization might be the more appropriate summarization of patient history as it would allow equitable comparisons between different patients.

Step 2. Now that there is a TP 304 associated with/attached to each patient in the TC, the N-dimensional History Representation 312 for each patient is generated on the basis of the MI present in the TP and the selected way of generating the History Representation. The N-dHRV is generated for each patient in the TC. The entire TC is now represented as a set of points (312) in the N-dimensional Euclidean space R^N. The TC along with all its history that is used for subtype derivation is mapped onto the N-dimensional Euclidean space R^N.

Step 3. The set of N-dHRV data points in R^N representing the entire training cohort allows sub-cohorts to be derived by segmenting the R^N dataset by a segmentation module 314 which outputs descriptions of the sub-cohorts (116).

One way of performing this operation is by using Unsupervised Learning methods from the fields of Machine Learning, Statistical Learning, Artificial Intelligence, Deep Learning or combinations thereof. Unsupervised Learning refers to the use of clustering algorithms to optimally split up R^N into subspaces. The number of resulting subspaces is either pre-specified by the user or optimally selected by the clustering algorithm, depending on the use case and/or the algorithm. There is a large variety of clustering algorithms. Examples include k-means, k-medians, Expectation Maximization clustering using Gaussian Mixture Models, Agglomerative Hierarchical Clustering, Density-Based Spatial Clustering of Applications with Noise (DBSCAN), Deep Embedded Clustering and many others. Each one of these algorithms can be used to derive MI's as described above. With some algorithms, the result in a number of hypersurfaces which serve as boundaries of the various subspaces.

Another way of performing the R^N segmentation is by using Supervised Learning algorithms, whereby a known outcome is available for each patient in training cohort and furnished to an algorithm along with the N-dHRV. Supervised Learning algorithms associate the N-dHRV with the known outcomes. In that way, the Supervised Learning algorithms provide implicit segmentation of R^N. There are possibilities for transforming such implicit segmentations into explicit segmentations such as those produced by Unsupervised Learning algorithms.

Additionally, other algorithms from the fields of Artificial Intelligence, Machine Learning, Deep Learning, Reinforcement Learning, Expert Systems, Bayesian Inference can be used to generate R^N segmentations.

Each R^N sub-segment contains a sub-cohort of the training cohort. The set of patients whose N-dHRV belongs to the i-th sub-segment constitute the i-th patient sub-cohort. Each R^N sub-segment is well defined by quantitative relationships between each variable in the N-dHRV. As each dimension of the N-dHRV represents actual phenotypic features of patients, the mathematical relationships which define the sub-segment in turn are a subtype definition (118) corresponding to that sub-cohort. A patient's phenotypic data at a certain time, when transformed into a point of the N-dHRV space, assigns the patient to one of the R^N sub-segments which have been derived based on the patients in the training cohort. Patient membership in a sub-segment of R^N amounts to membership of that patient in a specific subtype. N-dHRV sub-segments are by definition directly linked to patient subtypes. When there is a specific cohort of patients, then patient membership to subtypes result in patient sub-cohorts that correspond to each subtype.

A patient's membership in a specific subtype can be dynamic: this membership is associated not only with the patient/individual but also with the specific time period 304 over which the patient N-dHRV 312 is computed. Patient subtype membership can be time dependent: when the time period changes (for example, patient subtype membership is considered at different times with a fixed length of time period), the same individual patient may belong to different subtypes. This depends on the patient's history over the time period that is used to compute subtype membership at any given time.

Distributed Sub-Cohort Membership

In the description so far, an implicit assumption is that a given patient at a given time belongs to a single specific sub-cohort. However, this concept can be expanded to include distributed definition of sub-cohort membership. This expansion can be implemented using the concept of Membership Vectors (MV). The MV of a patient over a time period TP is a vector comprising as many elements as the number of sub-cohorts. Each element is a metric that represents the degree of membership to a specific sub-cohort. In the case where membership is strictly confined to a single sub-cohort, the MV could be designed to include just one element that is non-zero, the element that corresponds to the sub-cohort where the patient fully belongs. The rest of the elements could be 0. There are many ways to assign membership degrees. One example includes computing inverse Euclidean distance between the N-dHRV of the patient from each of a sub-cohort centroid. Another example is the outcome of probabilistic Unsupervised Learning models such as Gaussian Mixture Models or Dirichlet Mixture Models as examples. In the case of probabilistic clustering (occasionally also referred to as soft clustering), the resulting clusters are characterized by a combination of statistical measures such as center (mean) and covariance. The clusters are probability distributions and each patient is assigned a probability of belonging to (being characterized by) each cluster. In this case one could assign, deterministically, a single sub-cohort membership to the patient as the sub-cohort of highest probability of belonging to. There are many more ways in which MV can be computed. The advantage of distributed membership to sub-cohorts and subtypes is that we allow the analysis to consider proximity of the patient to multiple subtypes. This may allow a more complete view of the patient, by means of the multiple subtypes with which the patient has commonality.

Outcomes Per Sub-Cohort

As noted above in connection with the description of FIGS. 1 and 2, given a set of sub-cohorts for which outcome data is available for patients in those sub-cohorts, it is possible to compute sub-cohort level outcome statistics. The outcome data may represent actual outcomes or predicted outcomes or a combination of both. Thus, the sub-cohort outcome analysis module 130 can determine whether the sub-cohort level outcome statistics for one sub-cohort are different from sub-cohort level outcome statistics for other cohorts or known norms. As an example, if an average outcome of a first sub-cohort is different than an average outcome of a second sub-cohort, then there may be a characteristic of the patients in the first sub-cohort which suggests there is a medically-interesting subtype represented by this sub-cohort. By considering different kinds of outcome data and outcome statistics, the computer system can assist in exploring connections between subtypes and patient outcomes.

Turning now to FIG. 4, an example implementation of a sub-cohort outcome analysis module 130 will now be described. This module accesses data describing the sub-cohorts 114 and accesses outcome data 106. Given N sub-cohorts, a statistics processing module 400 accesses, for each sub-cohort, the available outcome data for each patient in the sub-cohort, to computes outcome statistic 402-1, . . . 402-N for the respective sub-cohort. Such sub-cohort level outcome statistics can include, but are not limited to, one or more of average outcomes, outcome rates, or expected average outcome, or any other sub-cohort level outcome statistics. A user interface module 404 can access the outcome statistics 402-*x*, 402-*y*, . . . , for one or more sub-cohorts x, y, . . . , to allow a user to visualize the outcome statistics. Such visualization may be provided by generating display data 406 including a graphical representation of such outcome statistics and presenting the display data on a display an interactive manner. For example, based on user input 408, the user interface module can select one or more sub-cohorts and the outcome statistics to be visualized. The user interface module may allow a visual, side-by-side comparison of the outcome statistics. The user interface module may perform computations to quantify this comparison. A result of such an analysis can be a selection of a sub-cohort that is medically interesting, by virtue of the fact that the sub-cohort has outcome statistics that are meaningfully different from the outcome statistics of other groups of patients, such as other sub-cohorts, the general population, or the training cohort, or other known norms for outcome statistics.

With this module 130, each sub-cohort can be associated with a certain rate of Medical Outcome. For example, the number of patients within a sub-cohort who will have a hypoglycemic hospitalization episode within 12 months after the end of the TP as a percentage of total patients in the sub-cohort defines a sub-cohort level medical outcome. This rate is called herein the Sub-Cohort Level Outcome. Possible outcomes include present or future medical episodes, development of new conditions, expenditures and other possible outcomes. Sub-Cohort Level Outcomes can be derived for multiple Medical Outcomes of interest.

Sub-Cohort Membership-Based Outcome Predictive Model

Sub-Cohort Level Outcomes are defined and computed based on the hypothesis that such outcomes are a property of the sub-cohort. The reasoning lies upon the very nature of generating sub-cohorts. Every patient in a sub-cohort has:
   a. similar phenotypic profile to every other patient in the same sub-cohort based on his/her medical history; and
   b. less similar profile to patients in different sub-cohorts than to patients in the same sub-cohort.

Consider now a patient-level predictive model where the predicted probability of an outcome for a specific patient is the sub-cohort based outcome of the sub-cohort in which the patient belongs. Since predictive models map a profile to a probability of outcome, sub-cohort based predictive modeling is expected to perform well as outcome predictor on the patient level.

To quantify and confirm predictive performance on a patient level the following steps can be performed:
   a. Split the TC into two sets, the Model Development Set (MDS) and the Out-of-Sample validation (OOS) set;
   b. Identify sub-cohorts in the manner described herein using only the patients in MDS;
   c. Compute the sub-cohort level outcome for each sub-cohort, based on the MDS data;
   d. For each patient in the OOS, identify the sub-cohort (referring to the sub-cohorts of item 3 above) to which the patient belongs, and assign the sub-cohort level outcome as the predicted/estimated outcome for the specific patient;
   e. Using the actual (known) outcome and the predicted/estimated outcome for each patient in OOS, compute predictive model Out-of-Sample performance.

More generally, such division of the TC into MDS and OOS can allow us to evaluate generalizability of any conclusions made using the derivation of sub-cohorts, subtypes and medically interesting subtypes. For example, if a certain medical instance enjoys high relative prevalence within a certain sub-cohort in relation to the rest of the MDS, one can use the corresponding sub-cohort of the OOS and deduce whether the same medical instance enjoys high relative prevalence. If so, this lends high confidence that the conclusion of the medical instance-related derivation and analysis within the MDS is generalizable to broader patient populations. It thus lends high confidence to the statement that the corresponding subtype is characterized by high relative prevalence of the certain medical instance. As another example, if a certain outcome is relatively higher within a certain sub-cohort in relation to the rest of the MDS, one can use the corresponding sub-cohort of the OOS and deduce whether said outcome is relatively high. If so, this lends high confidence that the conclusions of the outcome assessment and analysis within the MDS are generalizable to broader patient populations. It thus lends high confidence to the statement that the corresponding subtype is characterized by relatively high outcome.

All analyses described herein in the context of sub-cohorts can be performed in the context of the MDS for derivation and OOS for validation and assessment of generalizability, even if not explicitly stated herein.

Characterization of Sub-cohorts and Interpretability

This approach to classification of medical conditions provides ways to characterize cohorts of patients which allow human users to understand the special character of each sub-cohort in a transparent manner, unlike Machine Learning, Deep Learning, Artificial Intelligence solutions which result in opaque, "black box" solutions. To arrive at such a characterization, in the example implementation above, the prevalence of each medical instance within the sub-cohort is computed, relative to the prevalence of the medical instance in the entire training cohort. One way to define and compute such relative prevalence is to count the number of times that the medical instance is part of all patient data in the sub-cohort as well as the number of times that the medical instance is part of all patient data in the training cohort and divide the two numbers. There are several ways and computations that the relative prevalence of a medical instance in a sub-cohort can be evaluated.

A sub-cohort identified using the methodology described herein could have high relative prevalence in a few medical instances. Such medical instances with a high relative prevalence provide the special character of the sub-cohort. For example, a sub-cohort of diabetic patients may have high relative prevalence of insulin medications. Such sub-cohort thus includes the set of patients that are distinguished by the rest of the diabetic population due to their elevated intake of insulin medications.

Additionally, there could be cases where the unique character of a sub-cohort is provided by low relative prevalence in some medical instances, or by a mix of high relative prevalence in some medical instances and low relative prevalence in some other medical instances.

Additionally, the degree by which each sub-cohort differs by other sub-cohorts along the direction of any medical instance is precisely quantified at the sub-cohort level.

Assigning Interventions from a Library to Sub-Cohorts

The capability to interpret sub-cohorts on the basis of MI relative prevalence, allows medical experts to assign interventions on different sub-cohorts. Consider the example of the diabetic sub-cohort with high relative prevalence of insulin intake. It turns out that this sub-cohort is also associated with significantly higher than average rate of future hypoglycemic episodes. Therefore, action can be taken to alert these patients' physicians about their high intake of such medications and to consider the possibility of reducing their prescriptions of such. In some implementations, it might be identified that these patients correspond to certain physicians who tend to over prescribe such medications. In that case, action can be taken to advice these physicians to regulate their prescriptions.

Furthermore, in cases such as the elevated insulin intake sub-cohort, precise quantification of sub-cohorts may allow detailed guidelines as to the recommended quantities of medications that should be prescribed.

In the general case, possible interventions can be considered a Library of Medical Interventions. Such a Library can be literally and officially developed and maintained, or it can more abstractly indicate the collective expertise of medical professionals, researchers and experts in the field.

The capability to characterize and describe sub-cohorts in terms of MI prevalence allows medical experts to assign interventions specific to types and subtypes in order to manage patient health.

Additionally, the matching of high relative prevalence MIs and interventions could potentially be provided by an engineered Expert System designed and trained using methods from the fields of Artificial Intelligence.

Figure 7:
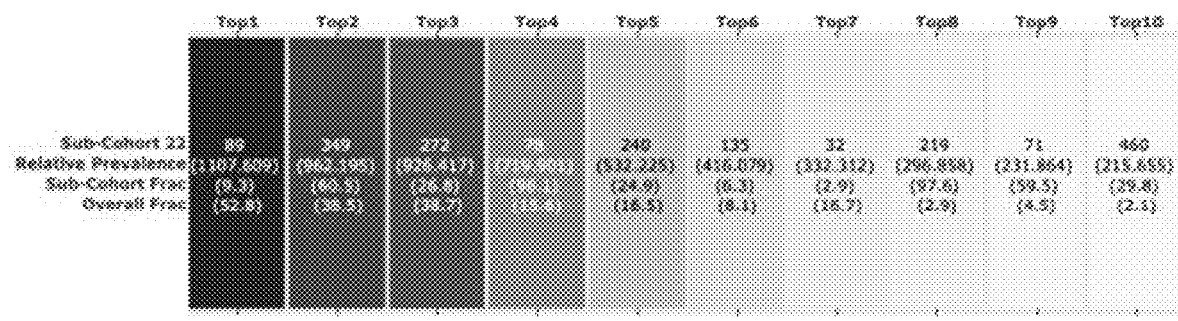
FIG. 7 is an illustrative drawing of example display data for an interactive user interface.
Figure 7:
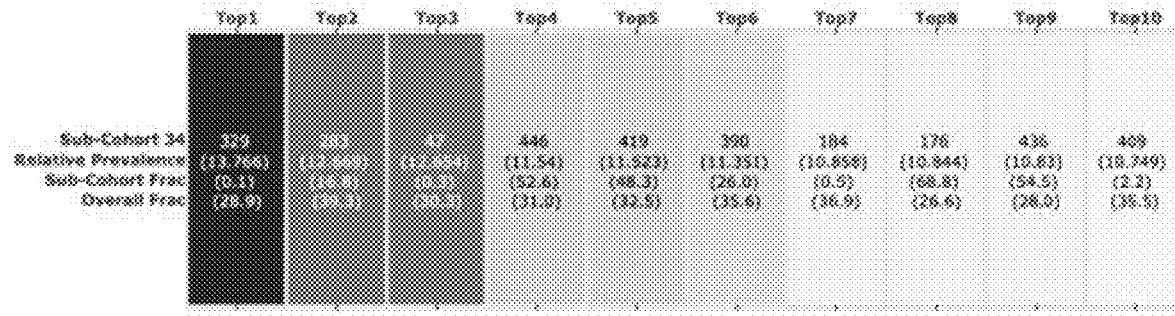
Figure 7:
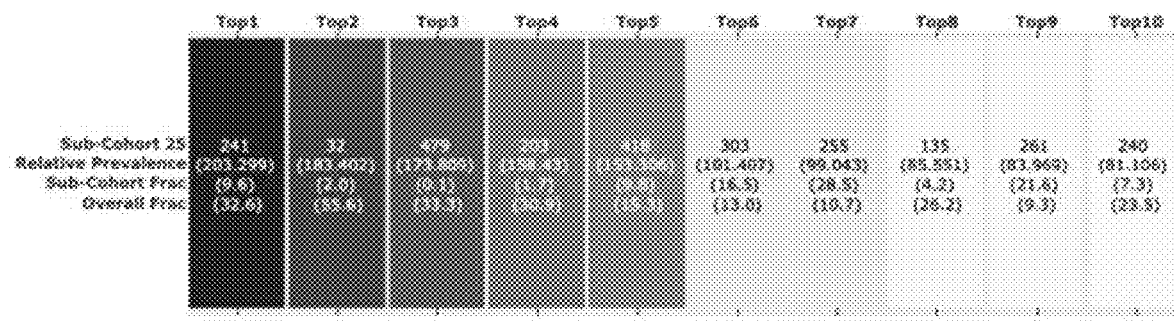
Figure 7:
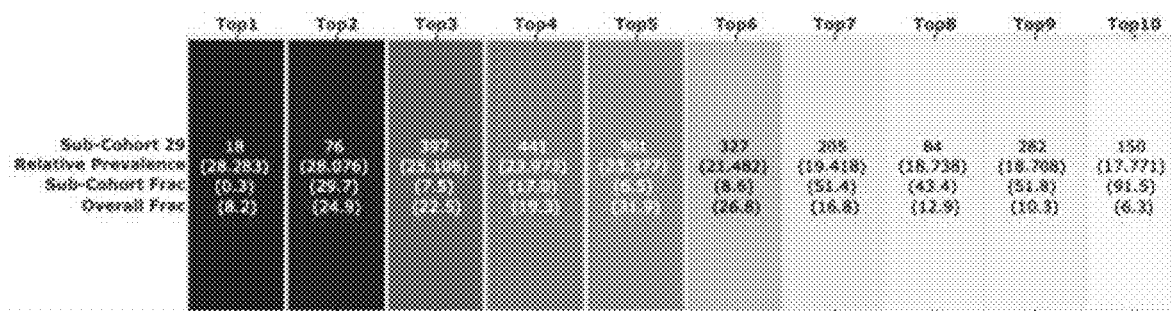

An example of display data 406 for an interactive user interface module 404 is illustrated in FIG. 7. In this snapshot of the interactive process, the user has selected a display of four different sub-cohorts of the Training Cohort (or, alternatively, the Model Development Set (MDS) or the Out-Of-Sample validation (OOS) Set). In this example, the Training Cohort is a set of patients with at least two Systemic Lupus Erythematosus diagnoses in their medical history. The outcome of interest is mortality over the 12 months immediately following the time period over which the medical data has been used to generate the patient vector. The system displays the Outcome Relative Prevalence (defined as the ratio of 1-year mortality rate within the sub-cohort divided by 1-year mortality rate within the Training Cohort). The user has selected to display 10 top Medical Instances, in descending order of Relative Prevalence of the Medical Instance (to be defined in the sequel) from the patient history among patients in each sub-cohort. Each horizontal block represents one sub-cohort. Each block includes 10 boxes, one per Medical Instance for the 10 MI's. At the top of each sub-cohort block is the count of patients in it. Each box includes 4 quantities: the code of the Medical Instance (e.g., 89 in the top left most box), the Relative Prevalence of the Medical Instance (prevalence, as in average number of occurrences of the MI in patient history, among patients in the sub-cohort divided by prevalence over the Training Cohort), the Sub-Cohort Frac(tion) (percentage of patients in the sub-cohort with at least one occurrence of the MI in their medical history) and the Overall Frac(tion) (percentage of patients in the Training Cohort with at least one occurrence of the MI in their medical history who belong to the sub-cohort). The intensity of the shading of the boxes is proportional to the Relative Prevalence of the Medical Instance. Although not shown in the image, the user is shown the composition of the corresponding Medical Instance (which medical events comprise the MI) when the user hovers the mouse over a box. This display allows the user to gain insights on sub-cohorts, identify sub-cohorts for further validation, and ultimately decide which of these sub-cohorts correspond to medically interesting subtypes.

Identifying Sub-Cohorts with Effective Treatments and Pathways

In the same way that a sub-cohort in which patients with an elevated risk of an adverse outcome can be identified, understood, quantified, and targeted for mitigating intervention, other sub-cohorts can be characterized by relatively desirable outcome rates. With such sub-cohorts, medical experts have the opportunity to identify medical or lifestyle practices with high relative prevalence within the sub-cohort. This allows the creation of hypotheses for optimal treatment which could be translatable to quantified protocols. A specific example is in the case of drug discovery, development, and testing. While current disease or health condition definitions are broad and heterogenous, as described earlier, when a drug or device or other treatment is developed and tested and submitted for regulatory approval, it may be required to list the specific indications for which it is intended to be used. A more clear, precise and mathematical description of subtypes and their relationship to specific outcomes permits a specific identification of the patients for whom a drug or treatment is being developed, for whom it will work, how well it will work, and with what risks. This improves both the regulatory process and how drugs, devices, procedures, and treatments are selected for individual patients.

Hierarchies of Subtypes

The training cohort (TC) has been divided in a number of sub-cohorts each of which includes patients with similar phenotypic characteristics. These sub-cohorts can be used to define patient subtypes. There may be some use cases where the number of generated subtypes is too high. One example includes cases where there is a multitude of subtypes with too small membership (number of patients) in cohorts of interest. The use case may include broader subtypes, each resulting in larger patient sub-cohorts, so as to apply a smaller number of interventions to larger numbers of patients. In such a case, a merging of subtypes is a solution. However, merging of subtypes should be carefully done in order to ensure that the subtypes that get merged are related to each other. In other words, the resulting merged subtypes should still include sets of patients that are similar to each other more than they are similar to patients in other merged subtypes.

The methodology can be altered to generate TC sub-cohorts (which are then used to define patient subtypes). One way to accomplish this objective is by using a methodology similar to the one used to generate MI's that are groups of codes.

One of these ways is to generate merged sub-cohorts of TC that are related to each other via frequent co-occurrence in patient histories. In fact, a patient history can be represented as a sequence of periods TP which may or may not overlap with each other. Each patient-TP combination is then mapped to a certain subtype among the set of subtypes that have already been generated, which can now be merged into broader subtypes (the patient during the period TP belongs to subtype k). A sequence of TP's is defined by the starting time of each TP. If the beginning of TP1 is earlier than the beginning of TP2, then TP1 precedes TP2 in the sequence. Note that the end of TP1 may be later in time than the beginning of TP2. In other words, TP1 and TP2 may overlap. In the above manner, sequences of TPs can be generated for each patient and these sequences are mapped to subtypes. Consequently, a patient history can be represented as a sequence of subtypes.

The co-occurrence relation-based methodologies also can be used to lead to the creation of MI's. One way is to use Hierarchical Clustering approaches, such as Agglomerative Hierarchical Clustering. Such methods generate a hierarchy of sub-segments in the N-dHRV and the number of R^N sub-segments, TC sub-cohorts, and patient subtypes can be varied.

Another concern could be that the number of subtypes is too low. Such is the case when an objective is to identify highly specific subtypes, resulting in relatively smaller sub-cohorts. For example, it is possible to find subtypes which are distinctly characterized by rare conditions or unusual excesses in intake of some medication, etc. In this case, one interest would be to have flexibility in allowing higher number of subtypes or sub-cohorts. Various techniques could be used for that. Hierarchical clustering approaches can be used either in the form of the Agglomerative Hierarchical Clustering algorithm or other techniques.

Mathematical, Quantitative Definition of Medical Conditions

Many associations between patient profile characteristics and outcomes are well understood directionally but not quantitatively. In the elevated insulin intake example, it is generally known that elevated insulin intake increases the risk of some individuals with Type II diabetes suffering a future hypoglycemic episode, but it is not well understood what more specifically and quantitatively defines and separates those most predisposed individuals and whether they constitute a discernible subtype of diabetes.

This methodology is applicable for identifying sub-cohorts within large patient populations as well as for typing or subtyping individuals to classify them within particular sub-cohorts for better understanding of the likelihood of progression, improvement, and discrete future outcomes, as well as potential efficacious treatments. Reliable associations can be provided due to processing large amounts of patient data.

The definition of each subtype is fully quantified. Given a patient and a TP, there is a deterministic way to assign subtype membership (whether single subtype or distributed). Each patient at each time has a subtype membership, this is a property of the patient. By way of his or her subtype membership, the patient is also associated with quantified subtype level outcome measures for various outcomes. Subtype membership is a precise mapping between patient profile and set of subtypes.

The combination of subtype membership and subtype outcome, as quantified using the TC sub-cohort outcome rates and statistics, allows measure driven medical conditions to be defined. A computer system classifies patients and their state of health or conditions or diseases in this way, by classifying patients in subtypes which are characterized by phenotypic, demographic, and genotypic characteristics and conditions as combination of subtype membership and subtype level outcome. Note that a variety of outcomes can be associated with each subtype. When a subtype has elevated rates of an adverse outcome, the combination works both as a diagnostic of the subtype-outcome condition as well as a way of assigning intervention protocol.

In summary, the combination of observations and events and biological findings and how they relate mathematically to each other and to the outcome is how the medical condition is defined. The medical condition definition provides the utility of treatment to mitigate adverse outcomes.

Mathematical, Quantitative Definition of Efficacious and Safe Drugs, Devices, Procedures, Treatments, Pathways and Protocols The methodology described herein is applicable at least for identifying patient subtypes and, consequently, sub-cohorts within large patient populations, with better understanding of potentially efficacious treatments that result in improved outcomes. By processing large amounts of patient data, the computer system can provide reliable associations between treatments and outcomes for subtypes of patients that exhibit similar patterns of symptoms, laboratory measurements, image generated understanding of underlying physiology, history of undergone procedures, demographic and genotypic characteristics while differing in certain components of their undergone treatment. These subtypes can be investigated for particular underlying biological processes for drug development. They can be targeted with available and new treatments for the specific impact of such treatments on known outcomes. They can be included in regulatory filings to specifically identify which patients a specific drug or device is intended to treat and with what anticipated outcomes. They can be incorporated into computer systems that receive or contain health information to identify a subtype for a specific patient, to help to plan or administer or approve any of an intervention, treatment, procedure, test, drug, device, pathway, lifestyle change. Subtypes also can be associated with a library of interventions which can be prescribed to patients with those subtypes. The same approach can be used to identify specific subtypes to target for drug development or other treatment or intervention development or matching. The computer system thus identifies medical protocols along with the patient subtypes that, when subjected to the protocol, show positive response. This approach to using mathematical relationships to describe types and subtypes of conditions or diseases also may make the regulatory approach to approval of drugs and devices clearer as treatments would be applicable to a specific subtype and approved to achieve a specific modification in the outcome of interest.

Representation of Subtype as a String

With a library of medical instances, each subtype can be uniquely, quantitatively, and mathematically characterized as a combination of a. a mapping which maps patient data for a patient into an N-dimensional patient vector and b. a subtype definition in the N-dimensional space.

An example characterization is the following. Each of the techniques described above to generate subtypes, provides a mathematical relationship that defines patient membership in the subtype. For example, in an implementation where membership is defined by minimum Euclidean proximity to a subtype centroid in $R^N$, this relationship is defined as the centroid whose Euclidean distance from the patient N-dHRV is lowest. In an implementation where membership is distributed, the degree of membership is identified as a function F of distance from subtype centroids in $R^N$. A suitable class of F functions includes, but is not limited to, scalar functions of scalars that are monotonically decreasing. In both these implementations, the centroid of a subtype is a single point in the N-dHRV which is derived by the methodology described herein. Different implementations from the above two examples would involve different membership mathematical relationships.

The membership mathematical relationship uses a set of quantities. In the above example, and in the case where M subtypes have been derived, the set of quantities includes N-coordinates for each one of the M subtype centroids. The set of all these quantities for the N coordinates for a centroid can be appropriately pulled together into a string which, along with the mathematical relationship that ties the quantities together, uniquely defines a subtype.

Figure 8:
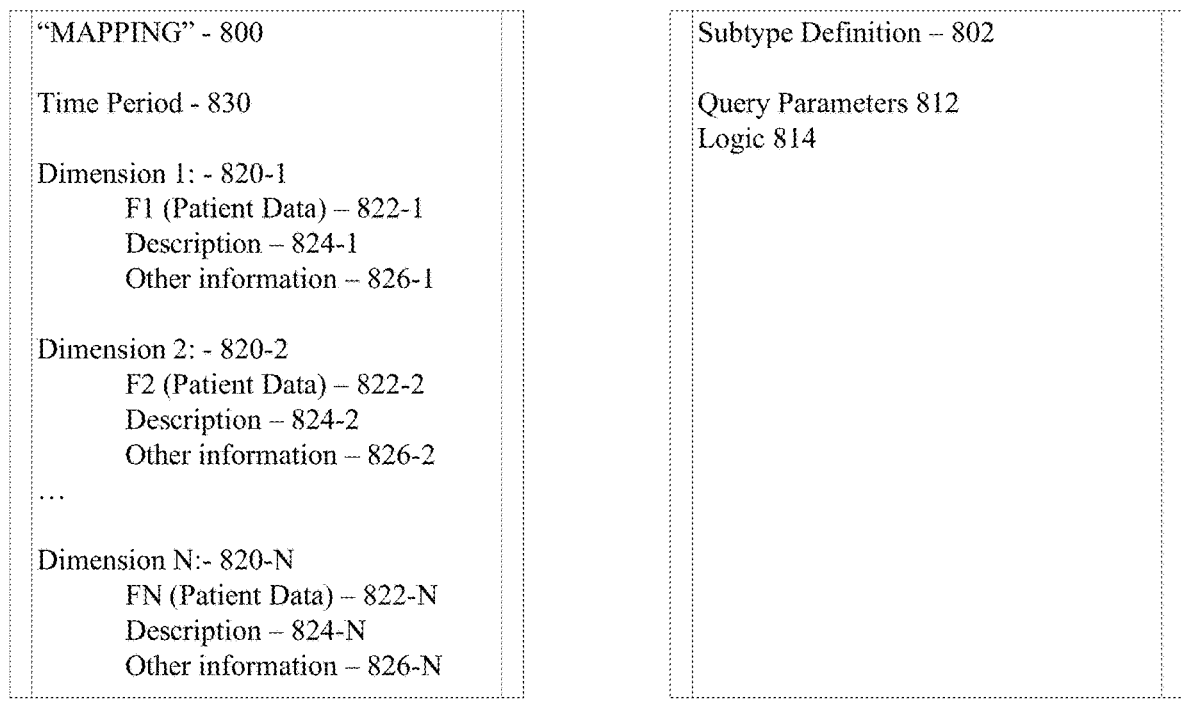
FIG. 8 is a drawing of an illustrative example of data structures characterizing a subtype.

Referring now to FIG. 8, an illustrative example of data structures for storing information in the classification system to represent subtypes will now be described. Generally, a subtype is characterized by a mapping 802 and a subtype definition 800. The subtype definition is a quantitative representation of the subtype which can be applied to an N-dimensional patient vector representing a patient to determine whether the patient belongs to the subtype. The mapping is a set of operations that transform patient data into the N-dimensional patient vector. The N-dimensional patient vector is a summary of the patient data. Each of the N dimensions represents a kind of data found in patient data. The value for any given dimension in the patient vector for a patient represents the prevalence of that kind of data in that patient's data. Given a mapping to transform patient data into a patient vector of N dimensions, and a subtype definition, patient data for any patient can be transformed, using the mapping, into a patient vector in the same N dimensions for which the subtype definition is defined, and it can be determined, by applying the subtype definition to the patient vector, whether that patient belongs to the subtype.

In FIG. 8, as a reference, an illustrative N-dimensional patient vector 840 is shown, having values for each of N dimensions 850-1, 850-2, . . . , 850-N.

The mapping 800 is represented by a data structure that stores, for each of N dimensions 820-1, 820-2, . . . , 820-N, data defining a respective operation (e.g. 822-1) to be applied to patient data that generates a value for a corresponding dimension (e.g., 850-1) of a patient vector. The format of the data defining the operation depends on the implementation, such as the nature of the patient data represented by each dimension, and how prevalence is determined from the patient data, examples of which are provided above. Other information can also be provided about each dimension, such as text for a human-readable description or explanation of the dimension (e.g., 824-1), or other information (e.g., 826-1). Data representing a time period 830 also can be stored if the mapping applied a time period to summarize patient data (as in some implementations described above).

The subtype definition 802 is represented by a data structure that stores query parameters 812 and logic 814. The logic 814 comprises any data that indicates an operation to be performed to process a patient vector. Query parameters 812 are any data that are used by the operation on the patient vector. The format of the query parameters and logic depends on the implementation. There is a wide variety of possible implementations of a data structure for the subtype definition. In one implementation, as described above, a result of identifying sub-cohorts is sets of coordinates of centroids describing each sub-cohort in the N dimensions. In some implementations, the query parameters 812 can include this set of centroids, and the logic 814 can include an indication of a similarity metric to be computed between a patient vector and each centroid. Example similarity metrics include, but are not limited to, Euclidean distance and squared Euclidean distance. A wide variety of measures of distance or similarity are available to be used. A patient can be considered belonging to the subtype with the centroid closest to the patient vector for the patient.

It should be understood that the data structures 800 and 802 are illustrated separately for ease of explanation, but can be implemented in a single data structure, or more data separate structures, depending on the implementation. There is a wide variety of possible implementations of data structures to represent mapping of patient data to patient vectors and to represent subtype definitions to apply to such patient vectors.

Subtype Membership Detection

After subtype definitions and associated mappings for medically interesting subtypes are stored as subtypes, this collection of subtypes becomes a classification system for medical conditions. The classification system for medical conditions is defined by the set of quantitative definitions of the subtypes. Each subtype has a subtype definition defined in an N-dimensional space which determines, given patient data for a patient, whether the patient belongs to the subtype. The subtype definition has an associated mapping defining how patient data is mapped to a patient vector representing the patient in the N-dimensional space in which the subtype is defined.

Figure 5:
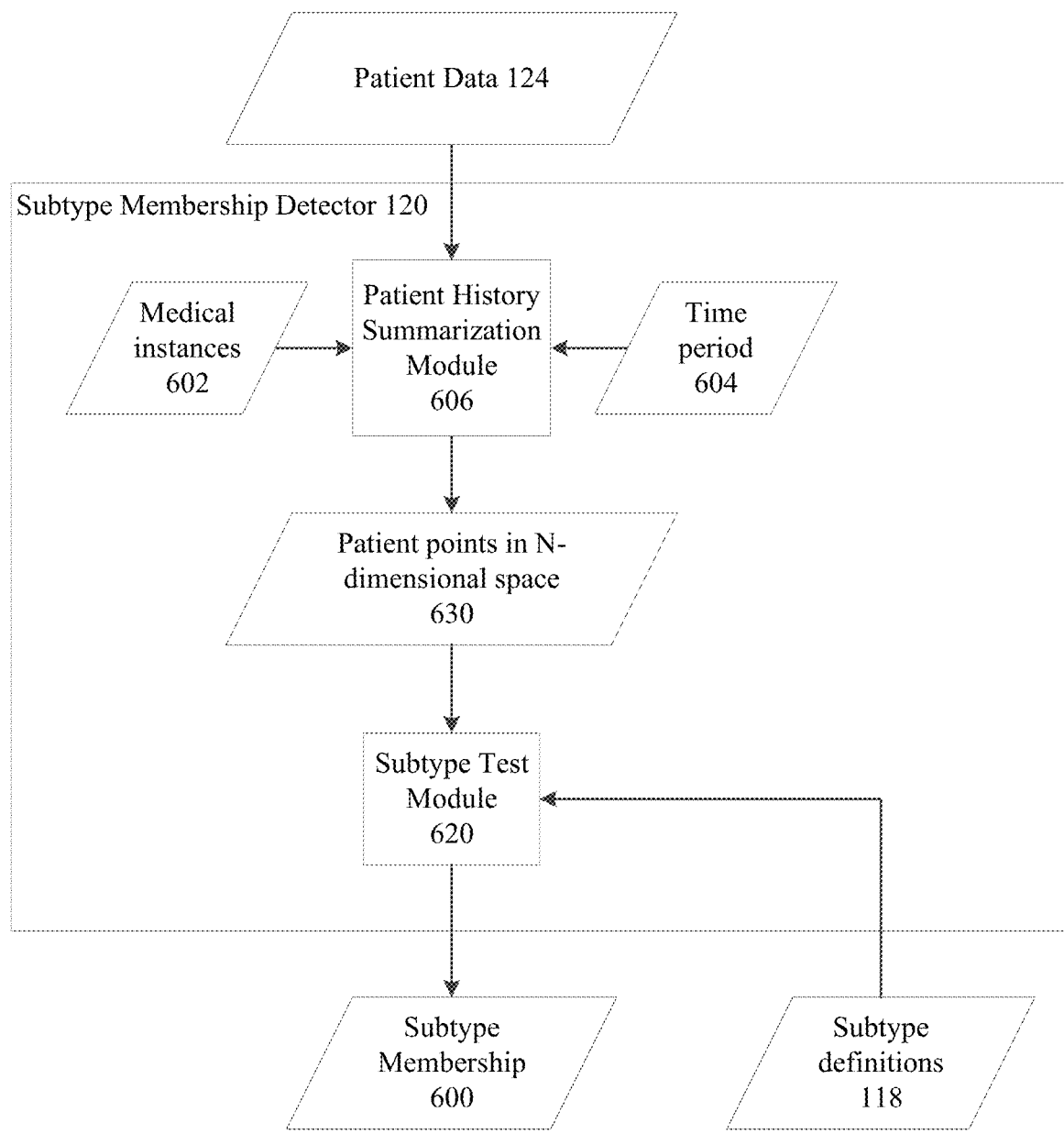
FIG. 5 is a data flow diagram describing an example implementation of a subtype membership detector.

Referring to FIG. 5, the subtype membership detector 120 of FIG. 1 will now be described in more detail. Note that the N dimensions of patient vectors, both what they represent and how values are computed, are the same in both the derivation and application of a subtype definition in N-dimensions. If the computer system uses an implementation such as shown in FIG. 3 which uses medical instances to derive subtypes, then a similar patient history summarization module 606, medical instances 602, and time period 604 are used to apply the subtype definition to other patient data 124. In FIG. 5, patient history summarization module 606, medical instances 602, and time period 604 map patient data for a patient into a point 630 in the N-dimensional space in which the subtype is defined. A subtype test module 620 applies the subtype definitions 118 to the point 630 to determine whether the patient represented by the point 630 is a member of the subtype. This indication of subtype membership is output at 600.

Reduction in Size of Subtype Definition

In an implementation such as described above, in which a subtype definition is represented as a string of data defining a centroid in N-dimensional space, the number of elements in this string may be very high. Often, there are important underlying patient characteristics that materially distinguish the identified, discovered subtype which may amount to a few key MI's and few key other patient characteristics. In cases like that, a definition of the subtype that involves only those material patient characteristics is a more functional, inclusive, and ultimately useful definition of the subtype. There could be many implementations for defining subtypes in this way. One implementation follows.

After a subtype has been discovered and identified using the above methodology, several defining MI's and other patient characteristics of the subtype can be isolated. Such isolation can use criteria such as:

a. Highest relative prevalence within the subtype (as statistically manifested within the corresponding sub-cohort of the TC); for each MI and other characteristic, the portion of patients and/or times in patient history and/or additional metrics of frequency that the characteristic occurs within the sub-cohort is computed and compared to the portion of patients and/or times in patient history and/or additional metrics of frequency that the characteristic occurs within the entire TC.

b. Highest prevalence within the subtype (as statistically manifested within the corresponding sub-cohort of the TC); for each MI and other characteristic, the count of patients and/or times in patient histories and/or additional metrics of frequency that the characteristic occurs within the sub-cohort is computed.

c. Lowest relative prevalence within the subtype, possibly combined with high overall prevalence within the overall TC (such would be the case that characterizes a subtype by the absence of an otherwise common characteristic within the overall TC, and the type of patient that the TC represents).

d. Criteria that combine metrics from Items a, b and c above. One example set of combined criteria could be those characteristics which belong to the top M % high relative prevalence set of MI's and other characteristics as well as the top P % high prevalence set of MI's and other characteristics. This set of characteristics could be augmented with other characteristics, for example, that are at the bottom K % relative prevalence but top L % prevalence within the overall TC.

In this implementation, the filtering of MI's and other characteristics results in a reduced number of characteristics that are used to identify the sub-cohorts. If an objective is to characterize subtypes based on a reduced set of MI's and other characteristics, then the description of a subtype can be confined to the reduced set of corresponding dimensions. Below are presented example implementations of dimensionality reduction:

Step 1. Retain the sub-cohort of TC which corresponds to the subtype that was identified in the N-dHRV.

Step 2. Retain the set of reduced number of important characteristics. Let this be a number of N1 characteristics, where N1<N. This defines a N1-dHRV (the dimensions of which are a subset of dimensions of the N-dHRV), which sits in the R^N1 Euclidean space.

In one implementation, the following steps can follow:

Step 3: Produce the N1-dHRV representation of each patient in the sub-cohort that corresponds to identified subtype. Assign a label 1 to each one of these patients and associate that label 1 to their N1-dHRV.

Step 4: Produce the N1-dHRV representation of every other patient in TC (all but those of the sub-cohort that corresponds to the subtype of interest). Assign a label 0 to each one of these patients and associate that label 0 to their N1-dHRV.

Step 5: Steps 3 and 4 have produced a dataset in R^N1 which has labels 0 and 1. All the datapoints are projections of patient N-dHRVs to N1-dHRVs in the lower dimensional space R^N1 Label 1's are projections of the patients that belong to the discovered subtype. Label 0's are projections of every other patient. This allows a classifier to be trained in R^N1 which will serve as the classifier for the generated subtype in R^N1 (those N1 dimensions are the MI's and other characteristics along which the specific subtype differs the most from other patient subtypes). This classifier can be a good separator of the subtypes (in other words, it can have high classification performance).

Step 6: This classifier is now defining a meta-subtype as follows: every patient who is classified as the original subtype using the generated classifier, is said to belong to the meta-subtype.

Step 7: To confirm that the meta-subtype in N1 dimensional space is medically relevant in the same way that the subtype in N dimensions was, outcomes of interest are computed in both the patient sub-cohort that corresponds to the meta subtype as well as everyone else. There can be a significant difference in outcomes, if the entire process of reducing dimensionality has been executed appropriately.

Step 8: The meta-subtype is now the subtype of interest.

Step 9: The classifier which allows the meta-subtype to be defined using a mathematical description, from which a uniquely characterizing string of the meta-subtype can be derived. For example, a linear classifier with a bias term will be defined by its (N1+1) linear model coefficients along with a potential classification level cut-off which defines the meta-subtype.

In the above implementation, appropriate dataset divisions for classifier development and out-of-sample validations of classifier as well as meta-subtype are implied.

In some implementations, a clustering machine learning algorithm can be used to generate two clusters in the R^N1 space, with one of the two clusters defining the meta-subtype.

The following in an example. A defined population of patients with classically diagnosed systemic lupus erythematosus (SLE), for whom a broad, multi-year collection of medical facts was available (number of patients is 550,000), was processed in the manner described above. The processing yielded a library of 500 MIs that were in turn used to generate a set of 100 sub-cohorts comprised of patients grouped or distinguished by their subtypes. The resulting subtypes, in this case, are represented by a string of 50,000 total coordinates, along with the mathematical relationship of minimum proximity. Qualitatively, a medically trained observer can see that the subtypes differ in such ways as the prevalence of conditions such as glaucoma, kidney disease, and lower extremity vasculitis related effects.

In another implementation, a limited set of medical instances are identified (by a user or by automated analysis) which are in highest relative prevalence (or some other alternative metric) within a certain sub-cohort, which certain sub-cohort has relatively high (or low) outcome and it constitutes a medically interesting subtype. In that case, a subtype can be defined which includes all patients who have an elevated presence of the limited set of medical instances in their medical history. The level of elevated presence could be above certain value, including the possibility of hypothesizing a subtype including all patients who have counts over 0 in all or any of the medical instances in the limited set of medical instances. Subsequently, a sub-cohort can be generated with all patients in the training cohort who belong to the newly defined subtype. Within this sub-cohort, a measurement of one or more outcomes and an evaluation of such outcome or outcomes rates can follow. If it is deemed that any such outcome is higher or lower than corresponding outcome in the overall patient population, or in the training cohort, or in other sub-cohorts in the population, then the newly defined subtype could constitute a medically interesting subtype. If the training cohort has been separated in MDS (used to derive sub-cohorts and definitions of subtypes) and OOS (used to assess generalizability of MDS findings), then outcome can be evaluated on the MDS and OOS separately and if the outcomes follow similar trends of being relatively higher or relatively lower within both MDS and OOS, this provides higher confidence in the validity of the newly defined subtype as a medically-interesting subtype.

An example of a subtype characterized by a small number of medical instances and derived in the manner described above is now presented. In this example, the training cohort is a set of patients with at least two Systemic Lupus Erythematosus diagnoses in their medical history. The outcome of interest is mortality over the 12 months immediately following the time period over which the medical data has been used to generate the patient vector. The resulting sub-cohort from the analysis includes all patients who have total occurrence count greater than 0 in each of two medical instances, coded as Medical Instances 84 and 282, over a period of 1 year prior to the time of computation of subtype membership. The list of medical event codes which roll up to the each one of these medical instances are provided in the tables in Appendix I (MI84) and Appendix II (MI282), which form a part of this application and are hereby incorporated by reference. One can see that MI 84 includes a set of diagnosis and procedure codes related to heart condition. The MI 282 includes a set of diagnosis and procedure codes associated with providing special care or nursing services. The outcome for this sub-cohort (1-yr mortality rate) is 516% higher than 1-yr mortality rate among the entire training cohort. Therefore, it constitutes a medically interesting subtype.

Hypotheses

Using outcome data, the computer system also can assist users in exploring connections between subtypes and outcomes and develop hypotheses about outcomes for patients of a subtype. A hypothesis identifies a connection between a set of facts from patient data and a corresponding outcome and is relevant to explaining why patients in one sub-cohort exhibit different outcomes than patients in another sub-cohort. Such a hypothesis can be tested through further medical research.

Figure 6:
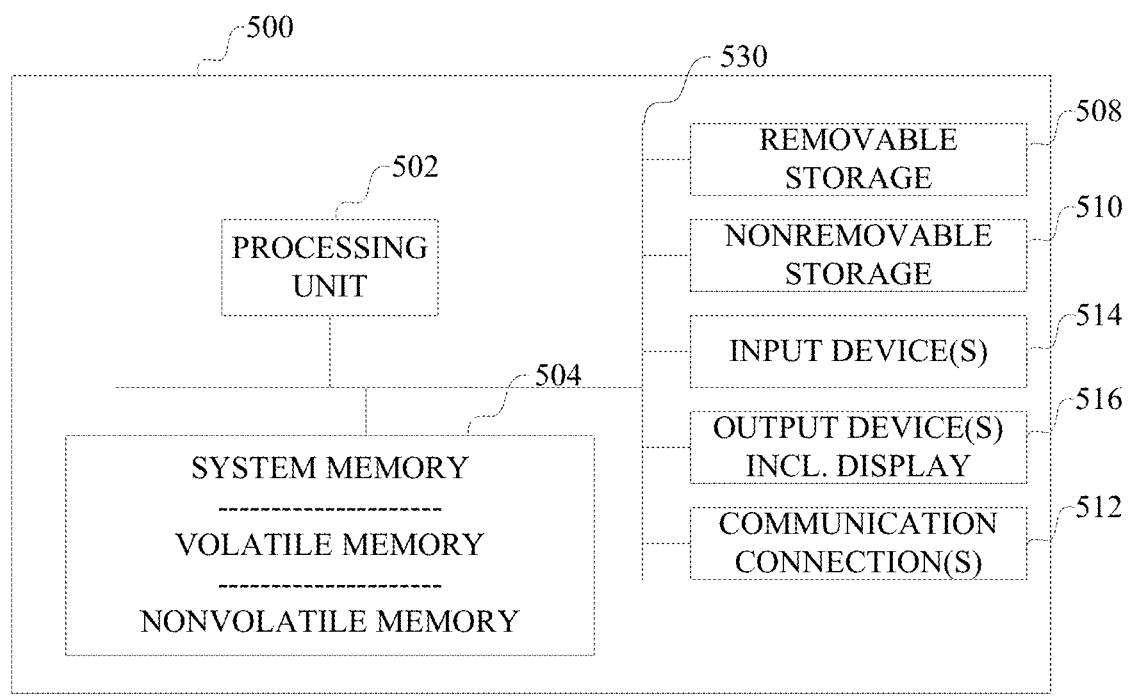
FIG. 6 is a block diagram of an example computer.

Having now described an example implementation, FIG. 6 illustrates an example of a computer with which components of the computer system of the foregoing description can be implemented. This is only one example of a computer and is not intended to suggest any limitation as to the scope of use or functionality of such a computer. The system described above can be implemented in one or more computer programs executed on one or more such computers as shown in FIG. 6.

The computer can be any of a variety of general purpose or special purpose computing hardware configurations. Some examples of types of computers that can be used include, but are not limited to, personal computers, game consoles, set top boxes, hand-held or laptop devices (for example, media players, notebook computers, tablet computers, cellular phones including but not limited to "smart" phones, personal data assistants, voice recorders), server computers, multiprocessor systems, microprocessor-based systems, programmable consumer electronics, networked personal computers, minicomputers, mainframe computers, and distributed computing environments that include any of the above types of computers or devices, and the like.

With reference to FIG. 6, a computer 500 includes a processing system comprising at least one processing unit 502 and at least one memory 504. The processing unit 502 can include multiple processing devices; the memory 504 can include multiple memory devices. A processing unit 502 comprises a processor which is logic circuitry which responds to and processes instructions to provide the functions of the computer. A processing device can include one or more processing cores (not shown) that are multiple processors within the same logic circuitry that can operate independently of each other. Generally, one of the processing units in the computer is designated as a primary processor, typically called the central processing unit (CPU). A computer can include coprocessors that perform specialized functions such as a graphical processing unit (GPU).

The memory 504 may include volatile computer storage devices (such as a dynamic or static random-access memory device), and non-volatile computer storage devices (such as a read-only memory or flash memory) or some combination of the two. A nonvolatile computer storage device is a computer storage device whose contents are not lost when power is removed. Other computer storage devices, such as dedicated memory or registers, also can be present in the one or more processors. The computer 500 can include additional computer storage devices (whether removable or non-removable) such as, but not limited to, magnetically-recorded or optically-recorded disks or tape. Such additional computer storage devices are illustrated in FIG. 6 by removable storage device 508 and non-removable storage device 510. Such computer storage devices 508 and 510 typically are nonvolatile storage devices. The various components in FIG. 6 are generally interconnected by an interconnection mechanism, such as one or more buses 530.

A computer storage device is any device in which data can be stored in and retrieved from addressable physical storage locations by the computer by changing state of the device at the addressable physical storage location. A computer storage device thus can be a volatile or nonvolatile memory, or a removable or non-removable storage device. Memory 504, removable storage 508 and non-removable storage 510 are all examples of computer storage devices. Computer storage devices and communication media are distinct categories, and both are distinct from signals propagating over communication media.

Computer 500 may also include communications connection(s) 512 that allow the computer to communicate with other devices over a communication medium.

Communication media typically transmit computer program instructions, data structures, program modules or other data over a wired or wireless substance by propagating a signal over the substance. By way of example, and not limitation, communication media includes wired media, such as metal or other electrically conductive wire that propagates electrical signals or optical fibers that propagate optical signals, and wireless media, such as any non-wired communication media that allows propagation of signals, such as acoustic, electromagnetic, electrical, optical, infrared, radio frequency and other signals.

Communications connections 512 are devices, such as a wired network interface, or wireless network interface, which interface with communication media to transmit data over and receive data from signal propagated over the communication media.

The computer 500 may have various input device(s) 514 such as a pointer device, keyboard, touch-based input device, pen, camera, microphone, sensors, such as accelerometers, thermometers, light sensors and the like, and so on. The computer 500 may have various output device(s) 516 such as a display, speakers, and so on. Such devices are well known in the art and need not be discussed at length here.

The various computer storage devices 508 and 510, communication connections 512, output devices 516 and input devices 514 can be integrated within a housing with the rest of the computer, or can be connected through various input/output interface devices on the computer, in which case the reference numbers 508, 510, 512, 514 and 516 can indicate either the interface for connection to a device or the device itself as the case may be. The various modules, tools, or applications, and data structures and flowcharts implementing the methodology described above, as well as any operating system, file system and applications, can be implemented using one or more processing units of one or more computers with one or more computer programs processed by the one or more processing units. A computer program includes computer-executable instructions and/or computer-interpreted instructions, such as program modules, which instructions are processed by one or more processing units in the computer. Generally, such instructions define routines, programs, objects, components, data structures, and so on, that, when processed by a processing unit, instruct or configure the computer to perform operations on data, or configure the computer to implement various components, modules or data structures.

In one aspect, an article of manufacture includes at least one computer storage medium, and computer program instructions stored on the at least one computer storage medium. The computer program instructions, when processed by a processing system of a computer, the processing system comprising one or more processing units and storage, configures the computer as set forth in any of the foregoing aspects and/or performs a process as set forth in any of the foregoing aspects.

Any of the foregoing aspects may be embodied as a computer system, as any individual component of such a computer system, as a process performed by such a computer system or any individual component of such a computer system, or as an article of manufacture including computer storage in which computer program instructions are stored and which, when processed by one or more computers, configure the one or more computers to provide such a computer system or any individual component of such a computer system.

APPENDIX I

| MI 84 | |
|---|---|
| code | name |
| I42.9_d_ICD10_Diagnosis | Cardiomyopathy, unspecified |
| I50.23_d_ICD10_Diagnosis | Acute on chronic systolic (congestive) heart failure |
| Z95.0_d_ICD10_Diagnosis | Presence of cardiac pacemaker |
| Z95.810_d_ICD10_Diagnosis | Presence of automatic (implantable) cardiac defibrillator |
| I42.0_d_ICD10_Diagnosis | Dilated cardiomyopathy |
| I47.2_d_ICD10_Diagnosis | Ventricular tachycardia |
| I48.92_d_ICD10_Diagnosis | Unspecified atrial flutter |
| I42.8_d_ICD10_Diagnosis | Other cardiomyopathies |
| I50.42_d_ICD10_Diagnosis | Chronic combined systolic (congestive) and diastolic (congestive) heart failure |
| I48.1_d_ICD10_Diagnosis | Persistent atrial fibrillation |
| I49.5_d_ICD10_Diagnosis | Sick sinus syndrome |
| I44.2_d_ICD10_Diagnosis | Atrioventricular block, complete |
| I44.7_d_ICD10_Diagnosis | Left bundle-branch block, unspecified |
| 93299_p_CPT | Interrogation device evaluation(s), (remote) up to 30 days; implantable cardiovascular physiologic monitor system or subcutaneous cardiac rhythm monitor system, remote data acquisition(s), receipt of transmissions and technician review, technical support and distribution of results |
| 93296_p_CPT | Interrogation device evaluation(s) (remote), up to 90 days; single, dual, or multiple lead pacemaker system, leadless pacemaker system, or implantable defibrillator system, remote data acquisition(s), receipt of transmissions and technician review, technical support and distribution of results |
| 93280_p_CPT | Programming device evaluation (in person) with iterative adjustment of the implantable device to test the function of the device and select optimal permanent programmed values with analysis, review and report by a physician or other qualified health care professional; dual lead pacemaker system |
| 93297_p_CPT | Interrogation device evaluation(s), (remote) up to 30 days; implantable cardiovascular physiologic monitor system, including analysis of 1 or more recorded physiologic cardiovascular data elements from all internal and external sensors, analysis, review(s) and report(s) by a physician or other qualified health care professional |
| I48.3_d_ICD10_Diagnosis | Typical atrial flutter |
| 93295_p_CPT | Interrogation device evaluation(s) (remote), up to 90 days; single, dual, or multiple lead implantable defibrillator system with interim analysis, review(s) and report(s) by a physician or other qualified health care professional |
| Z45.02_d_ICD10_Diagnosis | Encounter for adjustment and management of automatic implantable cardiac defibrillator |
| Z95.818_d_ICD10_Diagnosis | Presence of other cardiac implants and grafts |
| 93294_p_CPT | Interrogation device evaluation(s) (remote), up to 90 days; single, dual, or multiple lead pacemaker system, or leadless pacemaker system with interim analysis, review(s) and report(s) by a physician or other qualified health care professional |
| I49.01_d_ICD10_Diagnosis | Ventricular fibrillation |
| Z45.018_d_ICD10_Diagnosis | Encounter for adjustment and management of other part of cardiac pacemaker |
| 80162_p_CPT | Digoxin; total |
| 93451_p_CPT | Right heart catheterization including measurement(s) of oxygen saturation and cardiac output, when performed |
| T82.7XXD_d_ICD10_Diagnosis | Infection and inflammatory reaction due to other cardiac and vascular devices, implants and grafts, subsequent encounter |
| I42.2_d_ICD10_Diagnosis | Other hypertrophic cardiomyopathy |
| 93284_p_CPT | Programming device evaluation (in person) with iterative adjustment of the implantable device to test the function of the device and select optimal permanent programmed values with analysis, review and report by a physician or other qualified health care professional; multiple lead transvenous implantable defibrillator system |
| I44.1_d_ICD10_Diagnosis | Atrioventricular block, second degree |
| 93283_p_CPT | Programming device evaluation (in person) with iterative adjustment of the implantable device to test the function of the device and select optimal permanent programmed values with analysis, review and report by a physician or other qualified health care professional; dual lead transvenous implantable defibrillator system |
| I48.4_d_ICD10_Diagnosis | Atypical atrial flutter |
| 92960_p_CPT | Cardioversion, elective, electrical conversion of arrhythmia; external |
| K0606_p_HCPCS | Automatic external defibrillator, with integrated electrocardiogram analysis, garment type |
| Z45.010_d_ICD10_Diagnosis | Encounter for checking and testing of cardiac pacemaker pulse generator [battery] |
| 93290_p_CPT | Interrogation device evaluation (in person) with analysis, review and report by a physician or other qualified health care professional, includes connection, recording and disconnection per patient encounter; implantable cardiovascular physiologic monitor system, including analysis of 1 or more recorded physiologic cardiovascular data elements from all internal and external sensors |
| 93282_p_CPT | Programming device evaluation (in person) with iterative adjustment of the implantable device to test the function of the device and select optimal permanent programmed values with analysis, review and report by a physician or other qualified health care professional; single lead transvenous implantable defibrillator system |
| 33249_p_CPT | Insertion or replacement of permanent implantable defibrillator system, with transvenous lead(s), single or dual chamber |
| 33208_p_CPT | Insertion of new or replacement of permanent pacemaker with transvenous electrode(s); atrial and ventricular |
| 93289_p_CPT | Interrogation device evaluation (in person) with analysis, review and report by a physician or other qualified health care professional, includes connection, recording and disconnection per patient encounter; single, dual, or multiple lead transvenous implantable defibrillator system, including analysis of heart rhythm derived data elements |
| 93288_p_CPT | Interrogation device evaluation (in person) with analysis, review and report by a physician or other qualified health care professional, includes connection, recording and disconnection per patient encounter; single, dual, or multiple lead pacemaker system, or leadless pacemaker system |
| 93613_p_CPT | Intracardiac electrophysiologic 3-dimensional mapping (List separately in addition to code for primary procedure) |

APPENDIX I-continued

MI 84

| code | name |
|---|---|
| Z45.09_d_ICD10_Diagnosis | Encounter for adjustment and management of other cardiac device |
| 00537_p_CPT | Anesthesia for cardiac electrophysiologic procedures including radio frequency ablation |
| 93281_p_CPT | Programming device evaluation (in person) with iterative adjustment of the implantable device to test the function of the device and select optimal permanent programmed values with analysis, review and report by a physician or other qualified health care professional; multiple lead pacemaker system |
| 33225_p_CPT | Insertion of pacing electrode, cardiac venous system, for left ventricular pacing, at time of insertion of implantable defibrillator or pacemaker pulse generator (eg, for upgrade to dual chamber system) (List separately in addition to code for primary procedure) |
| 00530_p_CPT | Anesthesia for permanent transvenous pacemaker insertion |
| 93621_p_CPT | Comprehensive electrophysiologic evaluation including insertion and repositioning of multiple electrode catheters with induction or attempted induction of arrhythmia; with left atrial pacing and recording from coronary sinus or left atrium (List separately in addition to code for primary procedure) |
| 93653_p_CPT | Comprehensive electrophysiologic evaluation including insertion and repositioning of multiple electrode catheters with induction or attempted induction of an arrhythmia with right atrial pacing and recording, right ventricular pacing and recording (when necessary), and His bundle recording (when necessary) with intracardiac catheter ablation of arrhythmogenic focus; with treatment of supraventricular tachycardia by ablation of fast or slow atrioventricular pathway, accessory atrioventricular connection, cavo-tricuspid isthmus or other single atrial focus or source of atrial re-entry |
| 93662_p_CPT | Intracardiac echocardiography during therapeutic/diagnostic intervention, including imaging supervision and interpretation (List separately in addition to code for primary procedure) |
| I42.6_d_ICD10_Diagnosis | Alcoholic cardiomyopathy |
| 93641_p_CPT | Electrophysiologic evaluation of single or dual chamber pacing cardioverter-defibrillator leads including defibrillation threshold evaluation (induction of arrhythmia, evaluation of sensing and pacing for arrhythmia termination) at time of initial implantation or replacement; with testing of single or dual chamber pacing cardioverter-defibrillator pulse generator |
| 93623_p_CPT | Programmed stimulation and pacing after intravenous drug infusion (List separately in addition to code for primary procedure) |
| 00534_p_CPT | Anesthesia for transvenous insertion or replacement of pacing cardioverter-defibrillator |
| 33210_p_CPT | Insertion or replacement of temporary transvenous single chamber cardiac electrode or pacemaker catheter (separate procedure) |
| C1892_p_HCPCS | Introducer/sheath, guiding, intracardiac electro-physiological, fixed-curve, peel-away |
| 93656_p_CPT | Comprehensive electrophysiologic evaluation including transseptal catheterizations, insertion and repositioning of multiple electrode catheters with induction or attempted induction of an arrhythmia including left or right atrial pacing/recording when necessary, right ventricular pacing/recording when necessary, and His bundle recording when necessary with intracardiac catheter ablation of atrial fibrillation by pulmonary vein isolation |
| I45.5_d_ICD10_Diagnosis | Other specified heart block |
| C1898_p_HCPCS | Lead, pacemaker, other than transvenous vdd single pass |
| 93279_p_CPT | Programming device evaluation (in person) with iterative adjustment of the implantable device to test the function of the device and select optimal permanent programmed values with analysis, review and report by a physician or other qualified health care professional; single lead pacemaker system or leadless pacemaker system in one cardiac chamber |
| D86.85_d_ICD10_Diagnosis | Sarcoid myocarditis |
| 93655_p_CPT | Intracardiac catheter ablation of a discrete mechanism of arrhythmia which is distinct from the primary ablated mechanism, including repeat diagnostic maneuvers, to treat a spontaneous or induced arrhythmia (List separately in addition to code for primary procedure) |
| C1882_p_HCPCS | Cardioverter-defibrillator, other than single or dual chamber (implantable) |
| T82.110A_d_ICD10_Diagnosis | Breakdown (mechanical) of cardiac electrode, initial encounter |
| C1733_p_HCPCS | Catheter, electrophysiology, diagnostic/ablation, other than 3d or vector mapping, other than cool-tip |
| T82.198A_d_ICD10_Diagnosis | Other mechanical complication of other cardiac electronic device, initial encounter |
| T82.111A_d_ICD10_Diagnosis | Breakdown (mechanical) of cardiac pulse generator (battery), initial encounter |
| 75572_p_CPT | Computed tomography, heart, with contrast material, for evaluation of cardiac structure and morphology (including 3D image postprocessing, assessment of cardiac function, and evaluation of venous structures, if performed) |
| V45.02_d_ICD9_Diagnosis | Automatic implantable cardiac defibrillator in situ |
| C1785_p_HCPCS | Pacemaker, dual chamber, rate-responsive (implantable) |
| 00410_p_CPT | Anesthesia for procedures on the integumentary system on the extremities, anterior trunk and perineum; electrical conversion of arrhythmias |
| C1777_p_HCPCS | Lead, cardioverter-defibrillator, endocardial single coil (implantable) |
| C1722_p_HCPCS | Cardioverter-defibrillator, single chamber (implantable) |
| 93620_p_CPT | Comprehensive electrophysiologic evaluation including insertion and repositioning of multiple electrode catheters with induction or attempted induction of arrhythmia; with right atrial pacing and recording, right ventricular pacing and recording, His bundle recording |
| 427.1_d_ICD9_Diagnosis | Paroxysmal ventricular tachycardia |
| 33241_p_CPT | Removal of implantable defibrillator pulse generator only |
| 93286_p_CPT | Peri-procedural device evaluation (in person) and programming of device system parameters before or after a surgery, procedure, or test with analysis, review and report by a physician or other qualified health care professional; single, dual, or multiple lead pacemaker system, or leadless pacemaker system |
| T82.120A_d_ICD10_Diagnosis | Displacement of cardiac electrode, initial encounter |
| 00093873901_m_NDC | Mexiletine HCl Oral Capsule 150 MG |
| 93657_p_CPT | Additional linear or focal intracardiac catheter ablation of the left or right atrium for treatment of atrial fibrillation remaining after completion of pulmonary vein isolation (List separately in addition to code for primary procedure) |
| 147.0_d_ICD10_Diagnosis | Re-entry ventricular arrhythmia |

APPENDIX I-continued

MI 84

| code | name |
|---|---|
| 33284_p_CPT | Removal of an implantable, patient-activated cardiac event recorder |
| 428.42_d_ICD9_Diagnosis | Chronic combined systolic and diastolic heart failure |
| 33216_p_CPT | Insertion of a single transvenous electrode, permanent pacemaker or implantable defibrillator |
| T46.2X5A_d_ICD10_Diagnosis | Adverse effect of other antidysrhythmic drugs, initial encounter |
| C1900_p_HCPCS | Lead, left ventricular coronary venous system |
| 93287_p_CPT | Peri-procedural device evaluation (in person) and programming of device system parameters before or after a surgery, procedure, or test with analysis, review and report by a physician or other qualified health care professional; single, dual, or multiple lead implantable defibrillator system |
| JO282_m_HCPCS | Injection, amiodarone hydrochloride, 30 mg |
| 33228_p_CPT | Removal of permanent pacemaker pulse generator with replacement of pacemaker pulse generator; dual lead system |
| 33244_p_CPT | Removal of single or dual chamber implantable defibrillator electrode(s); by transvenous extraction |
| C1895_p_HCPCS | Lead, cardioverter-defibrillator, endocardial dual coil (implantable) |
| 93650_p_CPT | Intracardiac catheter ablation of atrioventricular node function, atrioventricular conduction for creation of complete heart block, with or without temporary pacemaker placement |
| 33264_p_CPT | Removal of implantable defibrillator pulse generator with replacement of implantable defibrillator pulse generator; multiple lead system |
| 149.02_d_ICD10_Diagnosis | Ventricular flutter |
| A9560_p_HCPCS | Technetium tc-99m labeled red blood cells, diagnostic, per study dose, up to 30 millicuries |
| 93600_p_CPT | Bundle of His recording |
| T82.191A_d_ICD10_Diagnosis | Other mechanical complication of cardiac pulse generator (battery), initial encounter |
| 33270_p_CPT | Insertion or replacement of permanent subcutaneous implantable defibrillator system, with subcutaneous electrode, including defibrillation threshold evaluation, induction of arrhythmia, evaluation of sensing for arrhythmia termination, and programming or reprogramming of sensing or therapeutic parameters, when performed |
| 93462_p_CPT | Left heart catheterization by transseptal puncture through intact septum or by transapical puncture (List separately in addition to code for primary procedure) |
| T82.118A_d_ICD10_Diagnosis | Breakdown (mechanical) of other cardiac electronic device, initial encounter |
| 426.0_d_ICD9_Diagnosis | Atrioventricular block, complete |
| T82.199A_d_ICD10_Diagnosis | Other mechanical complication of unspecified cardiac device, initial encounter |
| 33262_p_CPT | Removal of implantable defibrillator pulse generator with replacement of implantable defibrillator pulse generator; single lead system |
| T82.190A_d_ICD10_Diagnosis | Other mechanical complication of cardiac electrode, initial encounter |
| 33233_p_CPT | Removal of permanent pacemaker pulse generator only |
| 33263_p_CPT | Removal of implantable defibrillator pulse generator with replacement of implantable defibrillator pulse generator; dual lead system |
| 93261_p_CPT | Interrogation device evaluation (in person) with analysis, review and report by a physician or other qualified health care professional, includes connection, recording and disconnection per patient encounter; implantable subcutaneous lead defibrillator system |
| 93640_p_CPT | Electrophysiologic evaluation of single or dual chamber pacing cardioverter-defibrillator leads including defibrillation threshold evaluation (induction of arrhythmia, evaluation of sensing and pacing for arrhythmia termination) at time of initial implantation or replacement; |
| 33235_p_CPT | Removal of transvenous pacemaker electrode(s); dual lead system |
| I45.3_d_ICD10_Diagnosis | Trifascicular block |
| 93609_p_CPT | Intraventricular and/or intra-atrial mapping of tachycardia site(s) with catheter manipulation to record from multiple sites to identify origin of tachycardia (List separately in addition to code for primary procedure) |
| 33340_p_CPT | Percutaneous transcatheter closure of the left atrial appendage with endocardial implant, including fluoroscopy, transseptal puncture, catheter placement(s), left atrial angiography, left atrial appendage angiography, when performed, and radiological supervision and interpretation |
| 33207_p_CPT | Insertion of new or replacement of permanent pacemaker with transvenous electrode(s); ventricular |
| 93622_p_CPT | Comprehensive electrophysiologic evaluation including insertion and repositioning of multiple electrode catheters with induction or attempted induction of arrhythmia; with left ventricular pacing and recording (List separately in addition to code for primary procedure) |
| 93654_p_CPT | Comprehensive electrophysiologic evaluation including insertion and repositioning of multiple electrode catheters with induction or attempted induction of an arrhythmia with right atrial pacing and recording, right ventricular pacing and recording (when necessary), and His bundle recording (when necessary) with intracardiac catheter ablation of arrhythmogenic focus; with treatment of ventricular tachycardia or focus of ventricular ectopy including intracardiac electro-physiologic 3D mapping, when performed, and left ventricular pacing and recording, when performed |
| V45.09_d_ICD9_Diagnosis | Other specified cardiac device in situ |
| 33223_p_CPT | Relocation of skin pocket for implantable defibrillator |
| 33222_p_CPT | Relocation of skin pocket for pacemaker |
| C1779_p_HCPCS | Lead, pacemaker, transvenous vdd single pass |
| C1896_p_HCPCS | Lead, cardioverter-defibrillator, other than endocardial single or dual coil(implantable) |
| 33215_p_CPT | Repositioning of previously implanted transvenous pacemaker or implantable defibrillator (right atrial or right ventricular) electrode |
| C2630_p_HCPCS | Catheter, electrophysiology, diagnostic/ablation, other than 3d or vector mapping, cool-tip |
| C1721_p_HCPCS | Cardioverter-defibrillator, dual chamber (implantable) |
| T82.837A_d_ICD10_Diagnosis | Hemorrhage due to cardiac prosthetic devices, implants and grafts, initial encounter |
| T82.847A_d_ICD10_Diagnosis | Pain due to cardiac prosthetic devices, implants and grafts, initial encounter |
| 33224_p_CPT | Insertion of pacing electrode, cardiac venous system, for left ventricular pacing, with attachment to previously placed pacemaker or implantable defibrillator pulse generator (including revision of pocket, removal, insertion, and/or replacement of existing generator) |
| 92961_p_CPT | Cardioversion, elective, electrical conversion of arrhythmia; internal (separate procedure) |
| 33212_p_CPT | Insertion of pacemaker pulse generator only; with existing single lead |
| 33213_p_CPT | Insertion of pacemaker pulse generator only; with existing dual leads |
| J1742_p_HCPCS | Injection, ibutilide fumarate, 1 mg |
| J1742_m_HCPCS | Injection, ibutilide fumarate, 1 mg |
| C1786_p_HCPCS | Pacemaker, single chamber, rate-responsive (implantable) |

APPENDIX I-continued

MI 84

| code | name |
| --- | --- |
| 93619_p_CPT | Comprehensive electrophysiologic evaluation with right atrial pacing and recording, right ventricular pacing and recording, His bundle recording, including insertion and repositioning of multiple electrode catheters, without induction or attempted induction of arrhythmia |
| 78494_p_CPT | Cardiac blood pool imaging, gated equilibrium, SPECT, at rest, wall motion study plus ejection fraction, with or without quantitative processing |
| 33229_p_CPT | Removal of permanent pacemaker pulse generator with replacement of pacemaker pulse generator; multiple lead system |
| 33234_p_CPT | Removal of transvenous pacemaker electrode(s); single lead system, atrial or ventricular |
| T82.119A_d_ICD10_Diagnosis | Breakdown (mechanical) of unspecified cardiac electronic device, initial encounter |
| T82.518A_d_ICD10_Diagnosis | Breakdown (mechanical) of other cardiac and vascular devices and implants, initial encounter |
| V53.32_d_ICD9_Diagnosis | Fitting and adjustment of automatic implantable cardiac defibrillator |
| 93724_p_CPT | Electronic analysis of antitachycardia pacemaker system (includes electrocardiogramarding, programming of device, induction and termination of tachycardia via implanted pacemaker, and interpretation of recordings) |
| 33206_p_CPT | Insertion of new or replacement of permanent pacemaker with transvenous electrode(s); atrial |
| 93612_p_CPT | Intraventricular pacing |
| T82.110D_d_ICD10_Diagnosis | Breakdown (mechanical) of cardiac electrode, subsequent encounter |
| 33217_p_CPT | Insertion of 2 transvenous electrodes, permanent pacemaker or implantable defibrillator |
| 33218_p_CPT | Repair of single transvenous electrode, permanent pacemaker or implantable defibrillator |
| 93793_p_CPT | Anticoagulant management for a patient taking warfarin, must include review and interpretation of a new home, office, or lab international normalized ratio (INR) test result, patient instructions, dosage adjustment (as needed), and scheduling of additional test(s), when performed |
| T82.190D_d_ICD10_Diagnosis | Other mechanical complication of cardiac electrode, subsequent encounter |
| 33214_p_CPT | Upgrade of implanted pacemaker system, conversion of single chamber system to dual chamber system (includes removal of previously placed pulse generator, testing of existing lead, insertion of new lead, insertion of new pulse generator) |
| 33240_p_CPT | Insertion of implantable defibrillator pulse generator only; with existing single lead |
| G8694_p_HCPCS | Left ventricular ejection fraction (lvef) <40% |
| 93260_p_CPT | Programming device evaluation (in person) with iterative adjustment of the implantable device to test the function of the device and select optimal permanent programmed values with analysis, review and report by a physician or other qualified health care professional; implantable subcutaneous lead defibrillator system |
| 33227_p_CPT | Removal of permanent pacemaker pulse generator with replacement of pacemaker pulse generator; single lead system |
| Z45.9_d_ICD10_Diagnosis | Encounter for adjustment and management of unspecified implanted device |
| L9900_p_HCPCS | Orthotic and prosthetic supply, accessory, and/or service component of another hcpcs \l\" code" |
| 425.5_d_ICD9_Diagnosis | Alcoholic cardiomyopathy |
| V45.00_d_ICD9_Diagnosis | Unspecified cardiac device in situ |
| V53.39_d_ICD9_Diagnosis | Fitting and adjustment of other cardiac device |
| V43.21_d_ICD9_Diagnosis | Organ or tissue replaced by other means, heart assist device |
| 42023010501_m_NDC | Brevital Sodium Injection Solution Reconstituted 500 MG |
| 996.04_d_ICD9_Diagnosis | Mechanical complication of automatic implantable cardiac defibrillator |
| 996.01_d_ICD9_Diagnosis | Mechanical complication due to cardiac pacemaker (electrode) |
| 996.61_d_ICD9_Diagnosis | Infection and inflammatory reaction due to cardiac device, implant, and graft |
| T46.2X1A_d_ICD10_Diagnosis | Poisoning by other antidysrhythmic drugs, accidental (unintentional), initial encounter |
| 93292_p_CPT | Interrogation device evaluation (in person) with analysis, review and report by a physician or other qualified health care professional, includes connection, recording and disconnection per patient encounter; wearable defibrillator system |
| B33.24_d_ICD10_Diagnosis | Viral cardiomyopathy |
| 33286_p_CPT | Removal, subcutaneous cardiac rhythm monitor |
| 93642_p_CPT | Electrophysiologic evaluation of single or dual chamber transvenous pacing cardioverter-defibrillator (includes defibrillation threshold evaluation, induction of arrhythmia, evaluation of sensing and pacing for arrhythmia termination, and programming or reprogramming of sensing or therapeutic parameters) |
| C2621_p_HCPCS | Pacemaker, other than single or dual chamber (implantable) |
| 996.09_d_ICD9_Diagnosis | Other mechanical complication of cardiac device, implant, and graft |
| 93603_p_CPT | Right ventricular recording |
| 93610_p_CPT | Intra-atrial pacing |
| 93602_p_CPT | Intra-atrial recording |
| T82.111D_d_ICD10_Diagnosis | Breakdown (mechanical) of cardiac pulse generator (battery), subsequent encounter |

APPENDIX II

MI 282

| code | name |
| --- | --- |
| G0156_p_HCPCS | Services of home health/hospice aide in home health or hospice settings, each 15 minutes |
| G0299_p_HCPCS | Direct skilled nursing services of a registered nurse (rn) in the home health or hospice setting, each 15 minutes |
| G0300_p_HCPCS | Direct skilled nursing services of a licensed practical nurse (lpn) in the home health or hospice setting, each 15 minutes |
| G0151_p_HCPCS | Services performed by a qualified physical therapist in the home health or hospice setting, each 15 minutes |
| 99308_p_CPT | Subsequent nursing facility care, per day, for the evaluation and management of a patient, which requires at least 2 of these 3 key components: An expanded problem focused interval history; An expanded problem focused examination; Medical decision making of low complexity. Counseling and/or coordination of care with other physicians, other qualified health care professionals, or agencies are provided consistent with the nature of the problem(s) and the patient's and/or family's needs. Usually, the patient is responding inadequately to therapy or has developed a minor complication. Typically, 15 minutes are spent at the bedside and on the patient's facility floor or unit. |
| 99309_p_CPT | Subsequent nursing facility care, per day, for the evaluation and management of a patient, which requires at least 2 of these 3 key components: A detailed interval history; A detailed examination; Medical decision making of moderate complexity. Counseling and/or coordination of care with other physicians, other qualified health care professionals, or agencies are provided consistent with the nature |

APPENDIX II-continued

MI 282

| code | name |
|---|---|
| | of the problem(s) and the patient's and/or family's needs. Usually, the patient has developed a significant complication or a significant new problem. Typically, 25 minutes are spent at the bedside and on the patient's facility floor or unit. |
| G0152_p_HCPCS | Services performed by a qualified occupational therapist in the home health or hospice setting, each 15 minutes |
| S9131_p_HCPCS | Physical therapy; in the home, per diem |
| S9123_p_HCPCS | Nursing care, in the home; by registered nurse, per hour (use for general nursing care only, not to be used when cpt codes 99500-99602 can be used) |
| P9604_p_HCPCS | Travel allowance one way in connection with medically necessary laboratory specimen collection drawn from home bound or nursing home bound patient; prorated trip charge |
| T1030_p_HCPCS | Nursing care, in the home, by registered nurse, per diem |
| Q5001_p_HCPCS | Hospice or home health care provided in patient's home/residence |
| A0428_p_HCPCS | Ambulance service, basic life support, non-emergency transport, (bls) |
| G0157_p_HCPCS | Services performed by a qualified physical therapist assistant in the home health or hospice setting, each 15 minutes |
| S9124_p_HCPCS | Nursing care, in the home; by licensed practical nurse, per hour |
| T1021_p_HCPCS | Home health aide or certified nurse assistant, per visit |
| P9603_p_HCPCS | Travel allowance one way in connection with medically necessary laboratory specimen collection drawn from home bound or nursing home bound patient; prorated miles actually travelled |
| S9129_p_HCPCS | Occupational therapy, in the home, per diem |
| 99306_p_CPT | Initial nursing facility care, per day, for the evaluation and management of a patient, which requires these 3 key components: A comprehensive history; A comprehensive examination; and Medical decision making of high complexity. Counseling and/or coordination of care with other physicians, other qualified health care professionals, or agencies are provided consistent with the nature of the problem(s) and the patient's and/or family's needs. Usually, the problem(s) requiring admission are of high severity. Typically, 45 minutes are spent at the bedside and on the patient's facility floor or unit. |
| K0001_p_HCPCS | Standard wheelchair |
| E0260_p_HCPCS | Hospital bed, semi-electric (head and foot adjustment) with any type side rails, with mattress |
| 99307_p_CPT | Subsequent nursing facility care, per day, for the evaluation and management of a patient, which requires at least 2 of these 3 key components: A problem focused interval history; A problem focused examination; Straightforward medical decision making. Counseling and/or coordination of care with other physicians, other qualified health care professionals, or agencies are provided consistent with the nature of the problem(s) and the patient's and/or family's needs. Usually, the patient is stable, recovering, or improving. Typically, 10 minutes are spent at the bedside and on the patient's facility floor or unit. |
| G0471_p_HCPCS | Collection of venous blood by venipuncture or urine sample by catheterization from an individual in a skilled nursing facility (snf) or by a laboratory on behalf of a home health agency (hha) |
| T1001_p_HCPCS | Nursing assessment/evaluation |
| 99310_p_CPT | Subsequent nursing facility care, per day, for the evaluation and management of a patient, which requires at least 2 of these 3 key components: A comprehensive interval history; A comprehensive examination; Medical decision making of high complexity. Counseling and/or coordination of care with other physicians, other qualified health care professionals, or agencies are provided consistent |

APPENDIX II-continued

MI 282

| code | name |
|---|---|
| | with the nature of the problem(s) and the patient's and/or family's needs. The patient may be unstable or may have developed a significant new problem requiring immediate physician attention. Typically, 35 minutes are spent at the bedside and on the patient's facility floor or unit. |
| R54_d_ICD10_Diagnosis | Age-related physical debility |
| K0195_p_HCPCS | Elevating leg rests, pair (for use with capped rental wheelchair base) |
| Q0092_p_HCPCS | Set-up portable x-ray equipment |
| G0180_p_HCPCS | Physician certification for medicare-covered home health services under a home health plan of care (patient not present), including contacts with home health agency and review of reports of patient status required by physicians to affirm the initial implementation of the plan of care that meets patient's needs, per certification period |
| 99305_p_CPT | Initial nursing facility care, per day, for the evaluation and management of a patient, which requires these 3 key components: A comprehensive history; A comprehensive examination; and Medical decision making of moderate complexity. Counseling and/or coordination of care with other physicians, other qualified health care professionals, or agencies are provided consistent with the nature of the problem(s) and the patient's and/or family's needs. Usually, the problem(s) requiring admission are of moderate severity. Typically, 35 minutes are spent at the bedside and on the patient's facility floor or unit. |
| G0495_p_HCPCS | Skilled services of a registered nurse (rn), in the training and/or education of a patient or family member, in the home health or hospice setting, each 15 minutes |
| E0143_p_HCPCS | Walker, folding, wheeled, adjustable or fixed height |
| R26.0_d_ICD10 Diagnosis | Ataxic gait |
| 99349_p_CPT | Home visit for the evaluation and management of an established patient, which requires at least 2 of these 3 key components: A detailed interval history; A detailed examination; Medical decision making of moderate complexity. Counseling and/or coordination of care with other physicians, other qualified health care professionals, or agencies are provided consistent with the nature of the problem(s) and the patient's and/or family's needs. Usually, the presenting problem(s) are moderate to high severity. Typically, 40 minutes are spent face-to-face with the patient and/or family. |
| Z99.3_d_ICD10 Diagnosis | Dependence on wheelchair |
| R0070_p_HCPCS | Transportation of portable x-ray equipment and personnel to home or nursing home, per trip to facility or location, one patient seen |
| G0493_p_HCPCS | Skilled services of a registered nurse (rn) for the observation and assessment of the patient's condition, each 15 minutes (the change in the patient's condition requires skilled nursing personnel to identify and evaluate the patient's need for possible modification of treatment in the home health or hospice setting) |
| G0179_p_HCPCS | Physician re-certification for medicare-covered home health services under a home health plan of care (patient not present), including contacts with home health agency and review of reports of patient status required by physicians to affirm the initial implementation of the plan of care that meets patient's needs, per re-certification period |
| K0003_p_HCPCS | Lightweight wheelchair |
| G0496_p_HCPCS | Skilled services of a licensed practical nurse (lpn), in the training and/or education of a patient or family member, in the home health or hospice setting, each 15 minutes |

APPENDIX II-continued

MI 282

| code | name |
|---|---|
| 99316_p_CPT | Nursing facility discharge day management; more than 30 minutes |
| R0075_p_HCPCS | Transportation of portable x-ray equipment and personnel to home or nursing home, per trip to facility or location, more than one patient seen |
| G0153_p_HCPCS | Services performed by a qualified speech-language pathologist in the home health or hospice setting, each 15 minutes |
| 99348_p_CPT | Home visit for the evaluation and management of an established patient, which requires at least 2 of these 3 key components: An expanded problem focused interval history; An expanded problem focused examination; Medical decision making of low complexity. Counseling and/or coordination of care with other physicians, other qualified health care professionals, or agencies are provided consistent with the nature of the problem(s) and the patient's and/or family's needs. Usually, the presenting problem(s) are of low to moderate severity. Typically, 25 minutes are spent face-to-face with the patient and/or family. |
| G0155_p_HCPCS | Services of clinical social worker in home health or hospice settings, each 15 minutes |
| T1031_p_HCPCS | Nursing care, in the home, by licensed practical nurse, per diem |
| E0156_p_HCPCS | Seat attachment, walker |
| 99350_p_CPT | Home visit for the evaluation and management of an established patient, which requires at least 2 of these 3 key components: A comprehensive interval history; A comprehensive examination; Medical decision making of moderate to high complexity. Counseling and/or coordination of care with other physicians, other qualified health care professionals, or agencies are provided consistent with the nature of the problem(s) and the patient's and/or family's needs. Usually, the presenting problem(s) are of moderate to high severity. The patient may be unstable or may have developed a significant new problem requiring immediate physician attention. Typically, 60 minutes are spent face-to-face with the patient and/or family. |
| G0158_p_HCPCS | Services performed by a qualified occupational therapist assistant in the home health or hospice setting, each 15 minutes |
| E0630_p_HCPCS | Patient lift, hydraulic or mechanical, includes any seat, sling, strap(s) or pad(s) |
| G0159_p_HCPCS | Services performed by a qualified physical therapist, in the home health setting, in the establishment or delivery of a safe and effective physical therapy maintenance program, each 15 minutes |
| K0004_p_HCPCS | High strength, lightweight wheelchair |
| E0163_p_HCPCS | Commode chair, mobile or stationary, with fixed arms |
| K0007_p_HCPCS | Extra heavy duty wheelchair |
| S9127_p_HCPCS | Social work visit, in the home, per diem |
| 99315_p_CPT | Nursing facility discharge day management; 30 minutes or less |
| E1038_p_HCPCS | Transport chair, adult size, patient weight capacity up to and including 300 pounds |
| E0971_p_HCPCS | Manual wheelchair accessory, anti-tipping device, each |
| E0261_p_HCPCS | Hospital bed, semi-electric (head and foot adjustment), with any type side rails, without mattress |
| E0277_p_HCPCS | Powered pressure-reducing air mattress |
| 99304_p_CPT | Initial nursing facility care, per day, for the evaluation and management of a patient, which requires these 3 key components: A detailed or comprehensive history; A detailed or comprehensive examination; and Medical decision making that is straightforward or of low complexity, Counseling and/or coordination of care with other physicians, other qualified health care professionals, or agencies are provided consistent with the nature of the problem(s) and the patient's and/or family's needs. Usually, the problem(s) requiring admission are of low severity. Typically, 25 minutes are spent at the bedside and on the patient's facility floor or unit. |
| 99341_p_CPT | Home visit for the evaluation and management of a new patient, which requires these 3 key components: A problem focused history; A problem focused examination; and Straightforward medical decision making. Counseling and/or coordination of care with other physicians, other qualified health care professionals, or agencies are provided consistent with the nature of the problem(s) and the patient's and/or family's needs. Usually, the presenting problem(s) are of low severity. Typically, 20 minutes are spent face-to-face with the patient and/or family. |
| S8120_p_HCPCS | Oxygen contents, gaseous, 1 unit equals 1 cubic foot |
| G0162_p_HCPCS | Skilled services by a registered nurse (rn) for management and evaluation of the plan of care; each 15 minutes (the patient's underlying condition or complication requires an rn to ensure that essential non-skilled care achieves its purpose in the home health or hospice setting) |
| G0160_p_HCPCS | Services performed by a qualified occupational therapist, in the home health setting, in the establishment or delivery of a safe and effective occupational therapy maintenance program, each 15 minutes |
| 99347_p_CPT | Home visit for the evaluation and management of an established patient, which requires at least 2 of these 3 key components: A problem focused interval history; A problem focused examination; Straightforward medical decision making. Counseling and/or coordination of care with other physicians, other qualified health care professionals, or agencies are provided consistent with the nature of the problem(s) and the patient's and/or family's needs. Usually, the presenting problem(s) are self limited or minor. Typically, 15 minutes are spent face-to-face with the patient and/or family. |
| E0973_p_HCPCS | Wheelchair accessory, adjustable height, detachable armrest, complete assembly, each |
| E2601_p_HCPCS | General use wheelchair seat cushion, width less than 22 inches, any depth |
| S9128_p_HCPCS | Speech therapy, in the home, per diem |
| L89.151_d_ICD10_Diagnosis | Pressure ulcer of sacral region, stage 1 |
| G0181_p_HCPCS | Physician supervision of a patient receiving medicare covered services provided by a participating home health agency (patient not present) requiring complex and multidisciplinary care modalities involving regular physician development and/or revision of care plans, review of subsequent reports of patient status, review of laboratory and other studies communication (including telephone calls) with other health care professionals involved in the patient's care, integration of new information into the medical treatment plan and/or adjustment of medical therapy, within a calendar month, 30 minutes or more |
| 99334_p_CPT | Domiciliary or rest home visit for the evaluation and management of an established patient, which requires at least 2 of these 3 key components: A problem focused interval history; A problem focused examination; Straightforward medical decision making. Counseling and/or coordination of care with other physicians, other qualified health care professionals, or agencies are provided consistent with the nature of the problem(s) and the patient's and/or family's needs. Usually, the presenting problem(s) are self-limited or minor. Typically, 15 minutes are spent with the patient and/or family or caregiver. |
| K0739_p_HCPCS | Repair or nonroutine service for durable medical equipment other than oxygen equipment requiring |

APPENDIX II-continued

MI 282

| code | name |
|---|---|
| | the skill of a technician, labor component, per 15 minutes |
| G0154_p_HCPCS | Direct skilled nursing services of a licensed nurse (lpn or rn) in the home health or hospice setting, each 15 minutes |
| K0006_p_HCPCS | Heavy duty wheelchair |
| E0303_p_HCPCS | Hospital bed, heavy duty, extra wide, with weight capacity greater than 350 pounds, but less than or equal to 600 pounds, with any type side rails, with mattress |
| E1399_p_HCPCS | Durable medical equipment, miscellaneous |
| K0800_p_HCPCS | Power operated vehicle, group 1 standard, patient weight capacity up to and including 300 pounds |
| E0181_p_HCPCS | Powered pressure reducing mattress overlay/pad, alternating, with pump, includes heavy duty |
| E0990_p_HCPCS | Wheelchair accessory, elevating leg rest, complete assembly, each |
| E0149_p_HCPCS | Walker, heavy duty, wheeled, rigid or folding, any type |
| E0240_p_HCPCS | Bath/shower chair, with or without wheels, any size |
| E0978_p_HCPCS | Wheelchair accessory, positioning belt/safety belt/pelvic strap, each |
| K0823_p_HCPCS | Power wheelchair, group 2 standard, captains chair, patient weight capacity up to and including 300 pounds |
| 99344_p_CPT | Home visit for the evaluation and management of a new patient, which requires these 3 key components: A comprehensive history; A comprehensive examination; and Medical decision making of moderate complexity, Counseling and/or coordination of care with other physicians, other qualified health care professionals, or agencies are provided consistent with the nature of the problem(s) and the patient's and/or family's needs. Usually, the presenting problem(s) are of high severity. Typically, 60 minutes are spent face-to-face with the patient and/or family. |
| E0245_p_HCPCS | Tub stool or bench |
| E0185_p_HCPCS | Gel or gel-like pressure pad for mattress, standard mattress length and width |
| T2005_p_HCPCS | Non-emergency transportation; stretcher van |
| E2611_p_HCPCS | General use wheelchair back cushion, width less than 22 inches, any height, including any type mounting hardware |
| E0100_p_HCPCS | Cane, includes canes of all materials, adjustable or fixed, with tip |
| S0281_p_HCPCS | Medical home program, comprehensive care coordination and planning, maintenance of plan |
| 99600_p_CPT | Unlisted home visit service or procedure |
| K0052_p_HCPCS | Swingaway, detachable footrests, replacement only, each |
| E0910_p_HCPCS | Trapeze bars, a/k/a patient helper, attached to bed, with grab bar |
| E0951_p_HCPCS | Heel loop/holder, any type, with or without ankle strap, each |
| Q5002_p_HCPCS | Hospice or home health care provided in assisted living facility |
| G0161_p_HCPCS | Services performed by a qualified speech-language pathologist, in the home health setting, in the establishment or delivery of a safe and effective speech-language pathology maintenance program, each 15 minutes |
| E0912_p_HCPCS | Trapeze bar, heavy duty, for patient weight capacity greater than 250 pounds, free standing, complete with grab bar |
| E0271_p_HCPCS | Mattress, innerspring |
| E1226_p_HCPCS | Wheelchair accessory, manual fully reclining back, (recline greater than 80 degrees), each |
| E1230_p_HCPCS | Power operated vehicle (three or four wheel nonhighway) specify brand name and model number |
| E0144_p_HCPCS | Walker, enclosed, four sided framed, rigid or folding, wheeled with posterior seat |
| E0445_p_HCPCS | Oximeter device for measuring blood oxygen levels non-invasively |
| S5160_p_HCPCS | Emergency response system; installation and testing |
| E0105_p_HCPCS | Cane, quad or three prong, includes canes of all materials, adjustable or fixed, with tips |
| E2201_p_HCPCS | Manual wheelchair accessory, nonstandard seat frame, width greater than or equal to 20 inches and less than 24 inches |
| 99342_p_CPT | Home visit for the evaluation and management of a new patient, which requires these 3 key components: An expanded problem focused history; An expanded problem focused examination; and Medical decision making of low complexity. Counseling and/or coordination of care with other physicians, other qualified health care professionals, or agencies are provided consistent with the nature of the problem(s) and the patient's and/or family's needs. Usually, the presenting problem(s) are of moderate severity. Typically, 30 minutes are spent face-to-face with the patient and/or family |
| E1140_p_HCPCS | Wheelchair, detachable arms, desk or full length, swing away detachable footrests |
| E0940_p_HCPCS | Trapeze bar, free standing, complete with grab bar |
| E0961_p_HCPCS | Manual wheelchair accessory, wheel lock brake extension (handle), each |
| E0247_p_HCPCS | Transfer bench for tub or toilet with or without commode opening |
| E0265_p_HCPCS | Hospital bed, total electric (head, foot and height adjustments), with any type side rails, with mattress |
| 99510_p_CPT | Home visit for individual, family, or marriage counseling |
| E0705_p_HCPCS | Transfer device, any type, each |
| E2392_p_HCPCS | Power wheelchair accessory, solid (rubber/plastic) caster tire with integrated wheel, any size, replacement only, each |
| K0002_p_HCPCS | Standard hemi (low seat) wheelchair |
| E0244_p_HCPCS | Raised toilet seat |
| Q5009_p_HCPCS | Hospice or home health care provided in place not otherwise specified (nos) |
| E0301_p_HCPCS | Hospital bed, heavy duty, extra wide, with weight capacity greater than 350 pounds, but less than or equal to 600 pounds, with any type side rails, without mattress |
| 99318_p_CPT | Evaluation and management of a patient involving an annual nursing facility assessment, which requires these 3 key components: A detailed interval history; A comprehensive examination; and Medical decision making that is of low to moderate complexity. Counseling and/or coordination of care with other physicians, other qualified health care professionals, or agencies are provided consistent with the nature of the problem(s) and the patient's and/or family's needs. Usually, the patient is stable, recovering, or improving. Typically, 30 minutes are spent at the bedside and on the patient's facility floor or unit. |
| 99374_p_CPT | Supervision of a patient under care of home health agency (patient not present) in home, domiciliary or equivalent environment (eg, Alzheimer's facility) requiring complex and multidisciplinary care modalities involving regular development and/or revision of care plans by that individual, review of subsequent reports of patient status, review of related laboratory and other studies, communication (including telephone calls) for purposes of assessment or care decisions with health care professional(s), family member(s), surrogate decision maker(s) (eg, legal guardian) and/or key caregiver(s) involved in patient's care, integration of new information into the medical treatment plan and/or adjustment of medical therapy, within a calendar month; 15-29 minutes |
| E2361_p_HCPCS | Power wheelchair accessory, 22nf sealed lead acid battery, each, (e.g., gel cell, absorbed glassmat) |
| E0168_p_HCPCS | Commode chair, extra wide and/or heavy duty, stationary or mobile, with or without arms, any type, each |

APPENDIX II-continued

MI 282

| code | name |
|---|---|
| E0165_p_HCPCS | Commode chair, mobile or stationary, with detachable arms |
| 99324_p_CPT | Domiciliary or rest home visit for the evaluation and management of a new patient, which requires these 3 key components; A problem focused history; A problem focused examination; and Straightforward medical decision making. Counseling and/or coordination of care with other physicians, other qualified health care professionals, or agencies are provided consistent with the nature of the problem(s) and the patient's and/or family's needs. Usually, the presenting problem(s) are of low severity. Typically, 20 minutes are spent with the patient and/or family or caregiver |
| S3601_p_HCPCS | Emergency stat laboratory charge for patient who is homebound or residing in a nursing facility |
| E2208_p_HCPCS | Wheelchair accessory, cylinder tank carrier, each |
| E0241_p_HCPCS | Bath tub wall rail, each |
| E1039_p_HCPCS | Transport chair, adult size, heavy duty, patient weight capacity greater than 300 pounds |
| E2602_p_HCPCS | General use wheelchair seat cushion, width 22 inches or greater, any depth |
| A0420_p_HCPCS | Ambulance waiting time (als or bis), one half (1/2) hour increments |
| 99375_p_CPT | Supervision of a patient under care of home health agency (patient not present) in home, domiciliary or equivalent environment (eg, Alzheimer's facility) requiring complex and multidisciplinary care modalities involving regular development and/or revision of care plans by that individual, review of subsequent reports of patient status, review of related laboratory and other studies, communication (including telephone calls) for purposes of assessment or care decisions with health care professional(s), family member(s), surrogate decision maker(s) (eg, legal guardian) and/or key caregiver(s) involved in patient's care, integration of new information into the medical treatment plan and/or adjustment of medical therapy, within a calendar month; 30 minutes or more |
| E0147_HCPCS | Walker, heavy duty, multiple braking system, variable wheel resistance |
| E0159_p_HCPCS | Brake attachment for wheeled walker, replacement, each |
| S8121_p_HCPCS | Oxygen contents, liquid, 1 unit equals 1 pound |
| E2365_p_HCPCS | Power wheelchair accessory, u-1 sealed lead acid battery, each (e.g., gel cell, absorbed glassmat) |
| T4542_p_HCPCS | Incontinence product, disposable underpad, small size, each |
| E1150_p_HCPCS | Wheelchair, detachable arms, desk or full length swing away detachable elevating legrests |
| E0272_p_HCPCS | Mattress, foam rubber |
| G0372_p_HCPCS | Physician service required to establish and document the need for a power mobility device |
| E2366_p_HCPCS | Power wheelchair accessory, battery charger, single mode, for use with only one battery type, sealed or non-sealed, each |
| E0310_p_HCPCS | Bed side rails, full length |
| E1240_p_HCPCS | Lightweight wheelchair, detachable arms, (desk or full length) swing away detachable, elevating legrest |
| T1023_p_HCPCS | Screening to determine the appropriateness of consideration of an individual for participation in a specified program, project or treatment protocol, per encounter |
| S9110_p_HCPCS | Telemonitoring of patient in their home, including all necessary equipment; computer system, connections, and software; maintenance; patient education and support; per month |
| 99327_p_CPT | Domiciliary or rest home visit for the evaluation and management of a new patient, which requires these 3 key components: A comprehensive history; A comprehensive examination; and Medical decision making of moderate complexity. Counseling and/or coordination of care with other physicians, other qualified health care professionals, or agencies are provided consistent with the nature of the problem(s) and the patient's and/or family's needs. Usually, the presenting problem(s) are of high severity. Typically, 60 minutes are spent with the patient and/or family or caregiver. |
| E0255_p_HCPCS | Hospital bed, variable height, hi-lo, with any type side rails, with mattress |
| E0154_p_HCPCS | Platform attachment, walker, each |
| E2603_p_HCPCS | Skin protection wheelchair seat cushion, width less than 22 inches, any depth |
| E2202_p_HCPCS | Manual wheelchair accessory, nonstandard seat frame width, 24-27 inches |
| E0295_p_HCPCS | Hospital bed, semi-electric (head and foot adjustment), without side rails, without mattress |
| E0184_p_HCPCS | Dry pressure mattress |
| E1260_p_HCPCS | Lightweight wheelchair, detachable arms (desk or full length) swing away detachable footrest |
| 99337_p_CPT | Domiciliary or rest home visit for the evaluation and management of an established patient, which requires at least 2 of these 3 key components: A comprehensive interval history; A comprehensive examination; Medical decision making of moderate to high complexity. Counseling and/or coordination of care with other physicians, other qualified health care professionals, or agencies are provided consistent with the nature of the problem(s) and the patient's and/or family's needs. Usually, the presenting problem(s) are of moderate to high severity. The patient may be unstable or may have developed a significant new problem requiring immediate physician attention. Typically, 60 minutes are spent with the patient and/or family or caregiver. |
| 99339_p_CPT | Individual physician supervision of a patient (patient not present) in home, domiciliary or rest home (eg, assisted living facility) requiring complex and multidisciplinary care modalities involving regular physician development and/or revision of care plans, review of subsequent reports of patient status, review of related laboratory and other studies, communication (including telephone calls) for purposes of assessment or care decisions with health care professional(s), family member(s), surrogate decision maker(s) (eg, legal guardian) and/or key caregiver(s) involved in patient's care, integration of new information into the medical treatment plan and/ or adjustment of medical therapy, within a calendar month; 15-29 minutes |
| E1639_p_HCPCS | Scale, each |
| K0807_p_HCPCS | Power operated vehicle, group 2 heavy duty, patient weight capacity 301 to 450 pounds |
| E2612_p_HCPCS | General use wheelchair back cushion, width 22 inches or greater, any height, including any type mounting hardware |
| K0005_p_HCPCS | Ultralightweight wheelchair |
| E0274_p_HCPCS | Over-bed table |
| 99326_p_CPT | Domiciliary or rest home visit for the evaluation and management of a new patient, which requires these 3 key components: A detailed history; A detailed examination; and Medical decision making of moderate complexity Counseling and/or coordination of care with other physicians, other qualified health care professionals, or agencies are provided consistent with the nature of the problem(s) and the patient's and/or family's needs. Usually, the presenting problem(s) are of moderate to high severity. Typically, 45 minutes are spent with the patient and/or family or caregiver. |
| E0621_p_HCPCS | Sling or seat, patient lift, canvas or nylon |
| T2049_p_HCPCS | Non-emergency transportation; stretcher van, mileage; per mile |
| 96154_p_CPT | Health and behavior intervention, each 15 minutes, face-to-face; family (with the patient present) |
| G0164_p_HCPCS | Skilled services of a licensed nurse (lpn or rn), in the training and/or education of a patient or family member, in the home health or hospice setting, each 15 minutes |

APPENDIX II-continued

MI 282

| code | name |
| --- | --- |
| K0825_p_HCPCS | Power wheelchair, group 2 heavy duty, captains chair, patient weight capacity 301 to 450 pounds |
| A0384_p_HCPCS | Bls specialized service disposable supplies; defibrillation (used by als ambulances and bls ambulances in jurisdictions where defibrillation is permitted in bls ambulances) |
| A9281_p_HCPCS | Reaching/grabbing device, any type, any length, each |
| E0627_p_HCPCS | Seat lift mechanism, electric, any type |
| E0248_p_HCPCS | Transfer bench, heavy duty, for tub or toilet with or without commode opening |
| E0635_p_HCPCS | Patient lift, electric with seat or sling |
| E0246_p_HCPCS | Transfer tub rail attachment |
| T5999_p_HCPCS | Supply, not otherwise specified |
| E0155_p_HCPCS | Wheel attachment, rigid pick-up walker, per pair |
| E0243_p_HCPCS | Toilet rail, each |
| S9529_p_HCPCS | Routine venipuncture for collection of specimen(s), single home bound, nursing home, or skilled nursing facility patient |
| K0056_p_HCPCS | Seat height less than 17\or equal to or greater than 21\" for a high strength, lightweight, or ultralightweight wheelchair" |
| E1280_p_HCPCS | Heavy duty wheelchair, detachable arms (desk or full length) elevating legrests |
| K0816_p_HCPCS | Power wheelchair, group 1 standard, captains chair, patient weight capacity up to and including 300 pounds |
| E1290_p_HCPCS | Heavy duty wheelchair, detachable arms (desk or full length) swing away detachable footrest |
| K0733_p_HCPCS | Power wheelchair accessory, 12 to 24 amp hour sealed lead acid battery, each (e.g., gel cell, absorbed glassmat) |
| E1391_p_HCPCS | Oxygen concentrator, dual delivery port, capable of delivering 85 percent or greater oxygen concentration at the prescribed flow rate, each |
| K0801_p_HCPCS | Power operated vehicle, group 1 heavy duty, patient weight capacity 301 to 450 pounds |
| G0182_p_HCPCS | Physician supervision of a patient under a medicare-approved hospice (patient not present) requiring complex and multidisciplinary care modalities involving regular physician development and/or revision of care plans, review of subsequent reports of patient status, review of laboratory and other studies, communication (including telephone calls) with other health care professionals involved in the patient's care, integration of new information into the medical treatment plan and/or adjustment of medical therapy, within a calendar month, 30 minutes or more |
| E1130_p_HCPCS | Standard wheelchair, fixed full length arms, fixed or swing away detachable footrests |
| K0821_p_HCPCS | Power wheelchair, group 2 standard, portable, captains chair, patient weight capacity up to and including 300 pounds |
| E0250_p_HCPCS | Hospital bed, fixed height, with any type side rails, with mattress |
| E1092_p_HCPCS | Wide heavy duty wheel chair, detachable arms (desk or full length), swing away detachable elevating leg rests |
| K0053_p_HCPCS | Elevating footrests, articulating (telescoping), each |
| E0294_p_HCPCS | Hospital bed, semi-electric (head and foot adjustment), without side rails, with mattress |
| E0148_p_HCPCS | Walker, heavy duty, without wheels, rigid or folding, any type, each |
| A9280_p_HCPCS | Alert or alarm device, not otherwise classified |
| K0822_p_HCPCS | Power wheelchair, group 2 standard, sling/solid seat/back, patient weight capacity up to and including 300 pounds |
| E1031_p_HCPCS | Rollabout chair, any and all types with casters 5\or greater" |
| E1090_p_HCPCS | High strength lightweight wheelchair, detachable arms desk or full length, swing away detachable foot rests |
| E0305_p_HCPCS | Bed side rails, half length |
| E1093_p_HCPCS | Wide heavy duty wheelchair, detachable arms desk or full length arms, swing away detachable footrests |
| G0163_p_HCPCS | Skilled services of a licensed nurse (lpn or rn) for the observation and assessment of the patient's condition, each 15 minutes (the change in the patient's condition requires skilled nursing personnel to identify and evaluate the patient's need for possible modification of treatment in the home health or hospice setting) |
| E0158_p_HCPCS | Leg extensions for walker, per set of four (4) |

What is claimed is:

1. A computer system for encoding patient data for a plurality of patients into a respective ordered collection of features representing the medical facts for each patient in the plurality of patients, for input to a computational model, the computer system comprising:
   a processing system comprising a processing device and memory, wherein the processing device processes computer program instructions to perform operations;
   computer storage connected to the processing system and storing at least:
      a. patient data comprising data representing a respective plurality of medical events for each of a plurality of patients, wherein data representing a medical event comprises at least one field and a respective value for each field, and
      b. a library of medical instance definitions, wherein each medical instance definition comprises a respective mapping of data representing one or more medical events into data representing a respective medical instance, wherein the respective medical instance is a more general, less granular, more generic, or less specific representation of a medical fact about a patient than the one or more medical events; and
   computer program instructions which, when processed by the processing system, cause the processing system to perform operations to:
      access a data structure specifying, for each dimension of an N-dimensional vector, a respective medical instance definition from the library;
      for each patient in the plurality of patients, convert the data representing a respective plurality of medical events for the patient into a respective N-dimensional vector of medical instances for the patient, by, for each dimension of the N-dimensional vector, applying the respective medical instance definition specified by the data structure to the data representing medical events for the patient to generate a respective medical instance for the dimension; and
      transmitting the respective N-dimensional vectors for the patients as the ordered collection of features representing the patients to the computational model for training or classification.

2. The computer system of claim 1, wherein the computer storage further stores a quantitative definition for a subtype characterizing a medically interesting sub-cohort, wherein the quantitative definition comprises data indicative of the data structure specifying the respective medical instance definitions used to generate the N-dimensional vectors for the patients and a subtype definition, wherein the subtype definition comprises a data structure that stores logic indicating:
   a. an operation to be performed to process the respective N-dimensional vector for a patient to determine membership of the patient in the subtype, and
   b. parameters used by the operation.

3. The computer system of claim 2, wherein the computational model comprises computer program instructions which, when processed by the processing system, cause the processing system to perform operations to apply the operation and with the parameters specified by a subtype definition to one or more N-dimensional vectors for patients to determine whether the patients are members of the sub-cohort characterized by the subtype.

4. The computer system of claim 1, wherein data representing a medical event includes a time for the medical event.

5. The computer system of claim 4, wherein the respective N-dimensional vectors are generated based on data representing medical events within a specified time period.

6. The computer system of claim 1, wherein, for at least one medical instance definition applied to one or more medical events, the medical instance is a more general representation of a medical fact about a patient than the one or more medical events.

7. The computer system of claim 1, wherein, for at least one medical instance definition applied to one or more medical events, the medical instance is a less granular representation of a medical fact about a patient than the one or more medical events.

8. The computer system of claim 1, wherein, for at least one medical instance definition applied to one or more medical events, the medical instance is a more generic representation of a medical fact about a patient than the one or more medical events.

9. The computer system of claim 1, wherein, for at least one medical instance definition applied to one or more medical events, the medical instance is a less specific representation of a medical fact about a patient than the one or more medical events.

10. The computer system of claim 1, wherein there are fewer medical instances for representing medical facts for patients than medical events.

11. The computer system of claim 1, wherein medical facts for patients may be represented inconsistently in the patient data.

12. The computer system of claim 11, wherein the respective N-dimensional vectors for the patients have reduced inconsistency with respect to the medical events for the patients.

13. The computer system of claim 11, wherein the respective N-dimensional vectors for the patients have improved consistency with respect to the medical events for the patients.

14. The computer system of claim 1, wherein medical facts for patients may be represented with high dimensionality in the patient data.

15. The computer system of claim 14, wherein the respective N-dimensional vectors for the patients have reduced dimensionality with respect to the medical events for the patients.

16. The computer system of claim 1, wherein medical facts for patients may be represented with high specificity in the patient data.

17. The computer system of claim 16, wherein the respective N-dimensional vectors for the patients define an outcome-oriented generality with respect to the medical events for the patients.

18. The computer system of claim 1, wherein the respective N-dimensional vectors representing patients map the patients to respective points in an N-dimensional space.

19. The computer system of claim 1, wherein the library of medical instance definitions comprises an operation that replaces a plurality of medical events with a single medical instance.

20. The computer system of claim 19, wherein the operation that replaces the plurality of medical events with the single medical instance comprises an operation based on co-occurrence of the plurality of medical events in a patent history.

21. The computer system of claim 1, wherein the library of medical instance definitions comprises an operation that replaces a first medical event with a medical instance representing a second medical event more general than the first medical event.

22. The computer system of claim 21, wherein the first medical event comprises a first code in a hierarchy of codes and the medical instance comprises a second code more general in the hierarchy of codes than the first code.

23. The computer system of claim 1, wherein a medical instance definition comprises an operation performed on patient data that maps a medical event to a corresponding medical instance by generalizing specific types of medical events into a more general type of medical instance.

24. The computer system of claim 1, wherein a medical instance definition comprises an operation performed on patient data that maps a medical event to a corresponding medical instance by replacing different types of medical events that represent a same medical fact into a type of medical instance.

25. The computer system of claim 1, further comprising:
   computer program instructions which, when processed by the processing system, cause the processing system to perform operations to derive medical instances based on the patient data.

26. The computer system of claim 25, wherein derivation of medical instances is based on co-occurrence relations.

27. The computer system of claim 25, wherein derivation of medical instances is based on grouping codes which relate to the same condition.

28. The computer system of claim 1, wherein the library comprises data structures specifying, for each medical instance:
   a. a set of one or more medical events that are members of the medical instance;
   b. one or more operations used to process the set of medical events;
   c. a label or a key uniquely identifying the medical instance; and
   d. a human-readable description of the medical instance.

29. The computer system of claim 1, further comprising:
   computer program instructions which, when processed by the processing system, cause the processing system to perform operations to characterize a sub-cohort of patients based on the medical instances computed for the patients.

30. A computer system, comprising:
   a processing system comprising a processing device and memory, wherein the processing device processes computer program instructions to perform operations;

computer storage connected to the processing system and storing at least:
  a. patient data comprising data representing a respective plurality of medical events for each of a plurality of patients, wherein data representing a medical event comprises at least one field and a respective value for each field,
  b. a library of medical instance definitions, wherein each medical instance definition comprises a mapping of data representing one or more medical events into data representing a medical instance, wherein the medical instance is a more general, less granular, more generic, or less specific representation of a medical fact about a patient than the one or more medical events, and
  c. a quantitative definition for a subtype characterizing a medically interesting sub-cohort of patients, wherein patients within the sub-cohort can receive a medical treatment for the sub-cohort, wherein the quantitative definition comprises:
    i. a data structure specifying, for each dimension of an N-dimensional vector, a respective medical instance definition from the library for generating a value for the dimension,
    ii. an operation to be performed to process a respective N-dimensional vector for a patient to determine membership of the patient in the sub-cohort, and
    iii. parameters used by the operation; and
computer program instructions which, when processed by the processing system, cause the processing system to perform operations to:
access the data structure specifying the respective medical instance definitions,
for each patient in the plurality of patients, apply the medical instance definitions specified by the data structure to the respective data representing medical events for the patient to generate a respective N-dimensional vector of medical instances for the patient, and
process the respective N-dimensional vectors for the patients using the operation and parameters specified by the subtype definition to determine, for each of the patients, whether the patient is a member of the sub-cohort.

* * * * *

UNITED STATES PATENT AND TRADEMARK OFFICE
CERTIFICATE OF CORRECTION

| | | |
|---|---|---|
| PATENT NO. | : 12,224,072 B2 | Page 1 of 1 |
| APPLICATION NO. | : 18/414296 | |
| DATED | : February 11, 2025 | |
| INVENTOR(S) | : Constantinos Ioannis Boussios et al. | |

It is certified that error appears in the above-identified patent and that said Letters Patent is hereby corrected as shown below:

In the Specification

In Column 1, Line 16, change "Dec. 19, 2021." to -- Dec. 21, 2019, --.

In the Claims

In Column 48, Line 48, in Claim 1, change "library:" to -- library; --.

Signed and Sealed this
Fourth Day of November, 2025

John A. Squires
*Director of the United States Patent and Trademark Office*